(12) United States Patent
Keenan et al.

(10) Patent No.: US 7,238,679 B2
(45) Date of Patent: Jul. 3, 2007

(54) HETEROCYCLES AND USES THEREOF

(75) Inventors: Terence P. Keenan, Bay Shore, NY (US); William C. Shakespeare, Southborough, MA (US)

(73) Assignee: Ariad Pharmaceuticals, Inc., Cambridge, MA (US)

( * ) Notice: Subject to any disclaimer, the term of this patent is extended or adjusted under 35 U.S.C. 154(b) by 1 day.

(21) Appl. No.: 10/744,601

(22) Filed: Dec. 23, 2003

(65) Prior Publication Data

US 2004/0171586 A1    Sep. 2, 2004

Related U.S. Application Data

(60) Provisional application No. 60/436,036, filed on Dec. 23, 2002.

(51) Int. Cl.
| | |
|---|---|
| A61K 31/517 | (2006.01) |
| A61K 31/675 | (2006.01) |
| C07F 9/02 | (2006.01) |
| A01N 57/00 | (2006.01) |
| C07D 211/32 | (2006.01) |
| C07D 233/00 | (2006.01) |
| C07D 249/04 | (2006.01) |
| C07D 257/10 | (2006.01) |
| C07D 263/30 | (2006.01) |
| C07D 277/20 | (2006.01) |
| C07D 403/00 | (2006.01) |
| C07D 413/00 | (2006.01) |

(52) U.S. Cl. .............. 514/81; 514/266.3; 514/266.4; 544/244

(58) Field of Classification Search ............... 514/81, 514/266.3, 266.4; 544/244
See application file for complete search history.

(56) References Cited

U.S. PATENT DOCUMENTS 4,070,468 A * 1/1978 Hardtmann et al. .......... 514/82
6,153,617 A * 11/2000 Bridges .................. 514/228.2

FOREIGN PATENT DOCUMENTS

WO        97-38983     * 10/1997

* cited by examiner

*Primary Examiner*—James O. Wilson
*Assistant Examiner*—Tamthom N. Truong
(74) *Attorney, Agent, or Firm*—David L. Berstein

(57) ABSTRACT

Compounds of the following formula are disclosed:

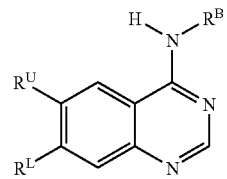

wherein $R^B$ is a substituted or unsubstituted aryl or heteroaryl moiety; at least one of $R^U$ and $R^L$ is a phosphorus-containing moiety, J, and the other of $R^U$ and $R^L$ is independently chosen from H; halogen; —CN; —NO$_2$; -J; —SO$_2$R; —SO$_2$NRR'; or —ZR$^J$, wherein each occurrence of Z is independently —O—, —S— or —NR— and each occurrence of $R^J$ is independently —R, —COR, —COOR or —CONRR'.

16 Claims, No Drawings

HETEROCYCLES AND USES THEREOF

The present application claims priority under 35 USC 119(e) to U.S. Provisional Application No. 60/436,036, filed Dec. 23, 2002, the entire contents of which are hereby incorporated by reference.

BACKGROUND OF THE INVENTION

The need to treat elusive and debilitating disorders such as cancer, rheumatoid arthritis, diseases involving undue inflammation or proliferation, osteoporosis and other diseases involving untoward bone resorption (e.g., Paget's Disease, primary and secondary hyperparathyroidism, humoral hypercalcemia of malignancy, and various cancers where bone resorption is increased), restenosis following coronary angioplasty, glomerulonephritis, glomerulosclerosis, liver cirrhosis, pulmonary fibrosis, disorders involving increased vascular permeability, and others, has led to extensive research on the mechanisms involved in disease initiation and/or progression and on the identification of new drugs which might interfere with those mechanisms.

Cellular signal transduction mediated by kinases is believed to play a key role in in cell proliferation, carcinogenesis and cell differentiation and in a wide variety of diseases, including those mentioned herein.

Several families of protein tyrosine kinases which have been implicated in human cancer and other diseases, include among many others, Src, Abl, Jak, Ack, Csk, Fak, Fes, Frk, Tec, and Syk. See. e.g., Blume-Jensen et al. Nature, 2001, 411, 355, and references cited therein.

Although some progress has been made towards developing therapeutic agents for a variety of disorders mentioned herein, there remains a need for new therapeutic agents which have desirable functional characteristics such as in vitro or in vivo potency, selectivity profile, ClogP, aqueous solubility, ability to penetrate cells, etc.,—or from an more global viewpoint, which have a beneficial therapeutic index, have a useful pharmacokinetic profile, have a desirable specificity of action, have reduced untoward side effects, may be given to patients who cannot well tolerate or do not respond sufficiently to existing therapies, and/or may be used in conjunction with other therapies.

DESCRIPTION OF THE INVENTION

1. General Description of Compounds of the Invention:

This invention provides a novel family of quinazolines (and pharmaceutically acceptable derivatives thereof that have a range of useful biological and pharmacological properties. These include compounds of general Formula I:

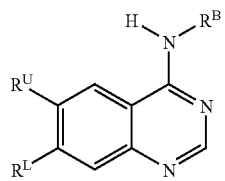

Formula I wherein:

$R^B$ is a substituted or unsubstituted aryl or heteroaryl moiety;

at least one of $R^U$ and $R^L$ is a phosphorus-containing moiety, J, which is covalently linked to the quinazoline ring through a carbon-phosphorous bond, e.g. as depicted in the following

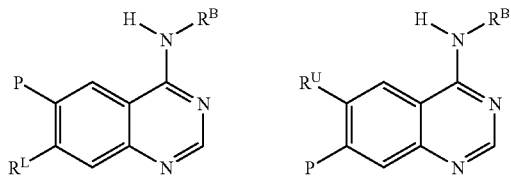

substructures in which each "P" is part of a moiety, J, described below:

and the other of $R^U$ and $R^L$ is independently chosen from H; halogen; —CN; —NO$_2$; —J; —SO$_2$R; —SO$_2$NRR'; or —ZR$^J$, wherein each occurrence of Z is independently —O—, —S— or —NR— and each occurrence of $R^J$ is independently —R, —COR, —COOR or —CONRR';

each occurrence of R, R', R", etc.(i.e., without further alphanumeric designation) is independently hydrogen, or an aliphatic, heteroaliphatic, aryl or heteroaryl moiety;

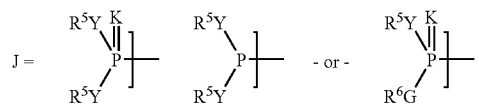

K is O or S;

each occurrence of Y is independently O, —S—, —NR—, or a chemical bond;

each occurrence of $R^5$ is independently an aliphatic, heteroaliphatic, aryl or heteroaryl moiety, or (except when attached directly to P, e.g., in YR$^5$ moieties in which Y is a chemical bond) $R^5$ may be H (Thus, in —P(O)(R$^5$)$_2$, for example, $R^5$ may not be H);

each occurrence of $R^6$ is independently $R^5$, —PK(YR$^5$)(YR$^5$), —SO$_2$(YR$^5$) or —(O)(YR$^5$) wherein two of the $R^5$ and/or $R^6$ moieties may be chemically linked to one another to form a ring;

each occurrence of G is independently —O—, —S—, —NR— or M$_X$;

each occurrence of $M_X$ is independently a 1–6 carbon aliphatic moiety; and in each of the foregoing groups each aliphatic or heteroaliphatic moiety may be branched or unbranched, cyclic or acyclic, substituted or unsubstituted, and may contain one or more electronically unsaturated bonds; and each aryl and heteroaryl moiety may be substituted or unsubstituted.

J moieties of special interest include those shown in Series 1:

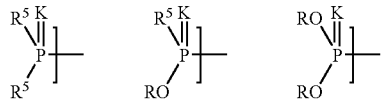

-continued

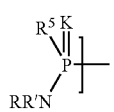 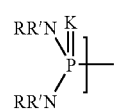 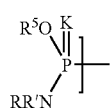

where K, R, R' and R⁵ are as defined above. Currently preferred J moieties are those in which K is oxygen, as are illustrated in exemplary compounds depicted below, including among others, moieties of any of the following structures:

(i)
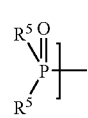

(ii)

(iii)

(iv)

(v)

(vi)

Examples of J moieties of type (i) showing illustrative substituted and unsubstituted R⁵ groups are shown below:

 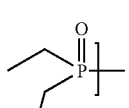 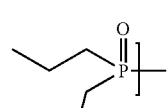

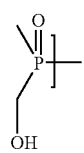

Examples of J moieties of type (i) illustrating heteroaliphatic or substituted R⁵ groups are shown below:

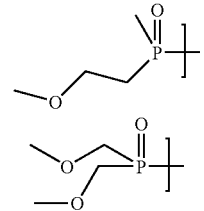

Further examples of type (i) illustrating R⁵ groups comprising heterocyclic moieties are shown below:

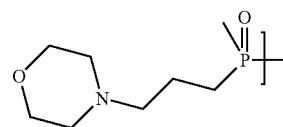

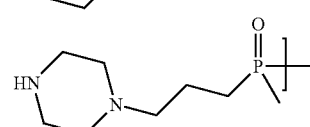

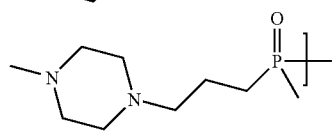

Illustrative analogous examples of type (ii) are shown below:

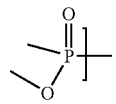 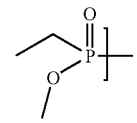

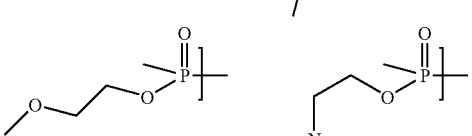

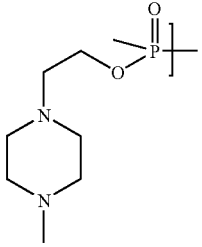 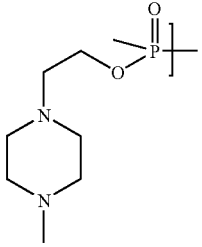

and others of types (i) through (vi) will be apparent to the practitioner.

Examples of $R^U$ and $R^L$ moieties, when $R^U$ or $R^L$ is not J, include moieties of the formula —OR⁷ or —NH(CO)R⁷, where R⁷ is a substituted or unsubstituted aliphatic, heteroaliphatic, aryl, or heteroaryl moiety. In such cases, substituted or unsubstituted aliphatic and heteroaliphatic R⁷ groups are of particular interest. Examples of such $R^U$ and $R^L$ moieties include MeO—, EtO—, MeOCH$_2$CH$_2$O—, MeOCH$_2$CH$_2$CH$_2$O—, CH$_2$=CHCH$_2$O—, CHCCH$_2$O— and $R^8M_XO$—, where $R^8$ is —J, —$ZR^J$ (including groups such as —OR, —NRR', —CN, —C(=NH)NH$_2$, and —NHC(=NH)NH$_2$), or a heterocylic moiety such as one of the following:

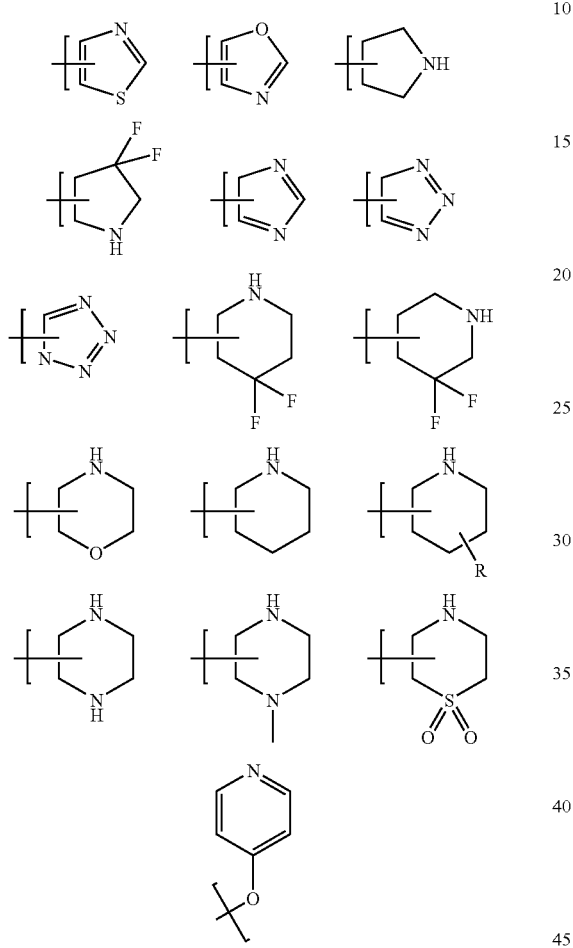

In such cases, moieties in which $M_X$ is a 2–4 carbon group are of particular interest, as illustrated by $R^U$ or $R^L$ moieties of the following structure, in which Q is O, NR or CHR:

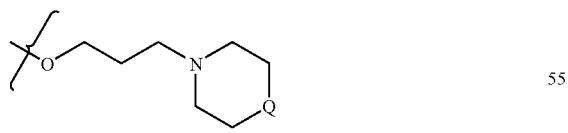

As previously noted, $R^B$ is a substituted or unsubstituted aryl or heteroaryl moiety. When substituted, $R^B$ can be monosubstituted or may contain substituents on any or all of the ring atoms available for substitution. Examples include aryl or heteroaryl moieties containing one or more of the following substituents: J; halogen; —CN; —NO$_2$; —R; or —$ZR^J$ (as those variables are previously defined). The following are illustrations of several such $R^B$ moieties:

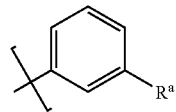 (a)

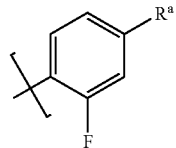 (b)

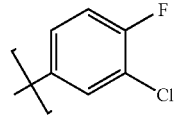 (c)

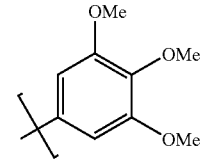 (d)

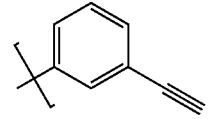 (e)

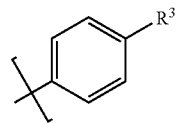 (f)

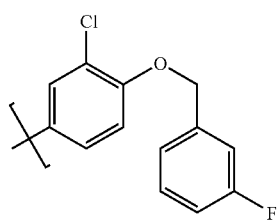 (g)

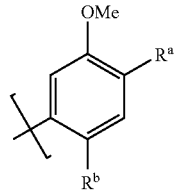 (h)

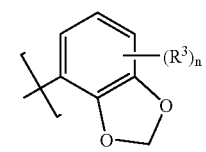 (i)

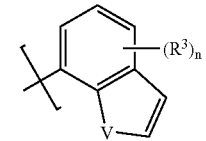 (j)

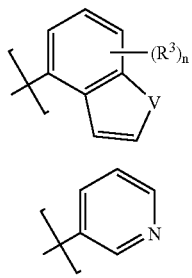
(k)

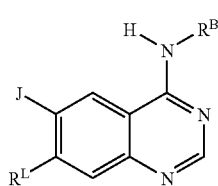
(l)

wherein each $R^a$ and $R^b$ is independently chosen from H, halogen or —$OR^J$; V is O or NH; n is 0, 1, 2 or 3; and each $R^3$ is halogen, trifluoromethyl, cyano, nitro, hydroxy, amino, carboxy, carbamoyl, (1–6C)alkyl, (2–8C)alkenyl, (2–8C) alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl(3–6C) alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

—$X^6$—$R^{11}$ wherein $X^6$ is a direct bond or is O or $N(R^{12})$, wherein $R^{12}$ is hydrogen or (1–6C)alkyl, and $R^{11}$ is halogeno-(1–6C) alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

—$X^7$-$Q^5$ wherein $X^7$ is a direct bond or is O, S, SO, $SO_2$, $N(R^{13})$, CO, $CH(OR^{13})$ $CON(R^{13})$, $N(R^{13})CO$, $SO_2N(R^{13})$, $N(R^{13})SO_2$, $QR^{13})_2O$, $C(R^{13})_2S$ or $N(R^{13})C(R^{13})_2$, wherein $R^{13}$ is hydrogen or (1–6C)alkyl, and $Q^5$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and any heterocyclyl group within $Q^5$ optionally bears 1 or 2 oxo or thioxo substituents; or a pharmaceutically-acceptable salt thereof.

2. Certain Featured Classes of Compounds of the Invention:

This new family of compounds includes the following two important classes of compounds:

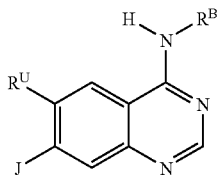
I-A

I-B

Subclasses of compounds of special interest include the following:
(1) Compounds of Formula I-A or I-B in which J is of type (i).
(2) Compounds of Formula I-A or I-B in which J is of type (ii).
(3) Compounds of Formula I-A or I-B in which J is of type (iii).
(4) Compounds of Formula I-A or I-B in which J is of type (iv).
(5) Compounds of Formula I-A or I-B in which J is of type (v).
(6) Compounds of Formula I-A or I-B in which J is of type (vi).
(7) Compounds of any of subclasses (1) through (6) in which $R^B$ is phenyl or an unsubstituted heteroaryl moiety.
(8) Compounds of any of subclasses (1) through (6) in which $R^B$ is an aryl or heteroaryl moiety bearing a single additional substituent.
(9) Compounds of any of subclasses (1) through (6) in which $R^B$ is an aryl or heteroaryl moiety bearing two additional substituents.
(10) Compounds of Formula I-A or I-B, including those of subclasses (1) through (6) in which $R^B$ is of type (c).
(11) Compounds of Formula I-A or I-B, including those of subclasses (1) through (6) in which $R^B$ is of type (e).
(12) Compounds of Formula I-A or I-B, including those of subclasses (1) through (6) in which $R^B$ is of type (f).
(13) Compounds of Formula I-A or I-B, including those of subclasses (1) through (6) in which $R^B$ is of type (h) and $R^a$ and $R^b$ are independently chosen from chloro, bromo and iodo.
(14) Compounds of Formula I-A or I-B, including those of subclasses (1) through (6) in which $R^B$ is of type (h) and both $R^a$ and $R^b$ are chloro.
(15) Compounds of Formula I-A or I-B, including those of subclasses (1) through (6) in which $R^B$ is of type (h) and $R^a$ is H.
(16) Compounds of Formula I-A or I-B, including those of subclasses (1) through (6) in which $R^B$ is of type (i).
(15) Compounds of Formula I-A or I-B, including those of subclasses (1) through (6) in which $R^B$ is of type (j) in which V is O.
(16) Compounds of Formula I-A or I-B, including those of subclasses (1) through (6) in which $R^B$ is of type (j) in which V is NH.
(17) Compounds of Formula I-A or I-B, including those of subclasses (1) through (6) in which $R^B$ is of type (k) in which V is O.
(18) Compounds of Formula I-A or I-B, including those of subclasses (1) through (6) in which $R^B$ is of type (j) in which V is NH.

Also of note are the following subclasses of compounds of Formula I-A or I-B:
the subclasses in which $R^B$ contains one or more substituents independently chosen from F; Cl; Br; I; —CN;

NNO$_2$; N$_3$; R$^5$; —GR$^5$; —CO(YR$^5$); —NR$^5$(YR$^5$); SO$_2$(YR$^5$); where each Y, G and R$^5$ are as previously defined;

the subclasses in which R$^B$ contains one or more substituents independently chosen from, F, Cl, Br, I, C$_{1-6}$alkyl, C$_{1-6}$alkenyl, C$_{1-6}$-alkynyl, C$_{3-8}$cycloalkyl, C$_{1-6}$-alkoxy, phenoxy, aryloxy, C$_{3-8}$cycloalkoxy, nitro, C$_{1-6}$-perfluoroalkyl, hydroxy, C$_{1-6}$acyloxy, —NH$_2$, —NH(C$_{1-6}$alkyl), —N(C$_{1-6}$alkyl)$_2$, —NH(C$_{3-8}$cycloalkyl), —N(C$_{3-8}$cycloalkyl)$_2$, hydroxymethyl, C$_{1-6}$acyl, cyano, azido, C$_{1-6}$thioalkyl, C$_{1-6}$sulfinylalkyl, C$_{1-6}$sulfonylalkyl, C$_{3-8}$thiocycloalkyl, C$_{3-8}$sulfinylcycloalkyl, C$_{3-8}$sulfonylcycloalkyl, mercapto, C$_{1-6}$alkoxycarbonyl, C$_{3-8}$cycloalkoxycarbonyl, C$_{2-4}$alkenyl, C$_{4-8}$cycloalkenyl, or C$_{2-4}$alkynyl;

the subclasses in which R$^B$ contains one or more substituents independently chosen from F, Cl, Br, I, hydroxyl, amino, or is an aliphatic or heteroaliphatic moiety, wherein the aliphatic or heteroaliphatic moiety is substituted or unsubstituted, cyclic or acyclic, linear or branched;

the subclasses in which R$^B$ contains one or more substituents independently chosen from F, Cl, Br, I, hydroxyl, substituted or unsubstituted amino, or is a substituted or unsubstituted alkyl, alkenyl or alkynyl moiety;

the subclasses in which R$^B$ contains one or more substituents independently chosen from F, Cl, Br, I, or a substituted or unsubstituted alkynyl group;

the subclasses in which R$^B$ contains one halogen;

the subclasses in which R$^B$ contains one bromine;

the subclasses in which R$^B$ contains one bromine located at the meta position;

the subclasses in which R$^B$ contains an F and a Cl;

the subclasses in which R$^B$ contains a meta Cl and a para F;

the subclasses in which one of R$^U$ and R$^L$ is ZR$^J$ and ZR$^J$ is a substituted or unsubstituted moiety selected from: hydroxy, amino, carboxy, carbamoyl, ureido, (C$_{1-4}$)alkoxycarbonyl, N-(C$_{1-4}$)alkylcarbamoyl, N,N-di-[(C$_{1-4}$)alkyl]carbamoyl, hydroxyamino, (C$_{1-4}$)alkoxyamino, (C$_{2-4}$)alkanoyloxyamino, trifluoromethoxy, (C$_{1-4}$)alkyl, 6-(C$_{1-4}$)alkoxy, 7-(C$_{1-4}$)alkoxy, (C$_{1-3}$)alkylenedioxy, (C$_{1-4}$)alkylamino, di-l[(C$_{1-4}$)alkyl]amino, pyrrolidin-1-yl, piperidino, morpholino, piperazin-1-yl, 4-(C$_{1-4}$)alkylpiperazin-1-yl, (C$_{1-4}$)alkylthio, (C$_{1-4}$)alkylsulphinyl, (C$_{1-4}$)alkylsulphonyl, bromomethyl, dibromomethyl, hydroxy-(C$_{1-4}$)alkyl, (C$_{2-4}$)alkanoyloxy-(C$_{1-4}$)alkyl, (C$_{1-4}$)alkoxy-(C$_{1-4}$)alkyl, carboxy-(C$_{1-4}$)alkyl, (C$_{1-4}$)alkoxycarbonyl-(C$_{1-4}$)alkyl, carbamoyl-(C$_{1-4}$)alkyl, N-(C$_{1-4}$)alkylcarbamoyl-(C$_{1-4}$)alkyl, N, N-di-[(C$_{1-4}$)alkyl]carbamoyl-(C$_{1-4}$)alkyl, amino-(C$_{1-4}$)alkyl, (C$_{1-4}$)alkylamino-(C$_{1-4}$)alkyl, di-[(C$_{1-4}$)alkyl]amino-(C$_{1-4}$)alkyl, piperidino-(C$_{1-4}$)alkyl, morpholino-(C$_{1-4}$)alkyl, piperazin-1-yl-(C$_{1-4}$) alkyl, 4-(C$_{1-4}$)alkylpiperazin-1-yl-(C$_{1-4}$) alkyl, hydroxy-(C$_{2-4}$)alkoxy-(C$_{1-4}$) alkyl, (C$_{1-4}$)alkoxy-(C$_{2-4}$)alkoxy-(C$_{1-4}$)alkyl, hydroxy-(C$_{2-4}$)alkylamino-(C$_{1-4}$)alkyl, (C$_{1-4}$)alkoxy-(C$_{2-4}$)alkylamino-(C$_{1-4}$)alkyl, (C$_{1-4}$)alkylthio-(C$_{1-4}$)alkyl, hydroxy-(C$_{2-4}$)alkylthio-(C$_{1-4}$)alkyl, (C$_{1-4}$)alkoxy-(C$_{2-4}$)alkylthio-(C$_{1-4}$)alkyl, phenoxy-(C$_{1-4}$) alkyl, anilino-(C$_{1-4}$)alkyl, phenylthio-(C$_{1-4}$)alkyl, cyano-(C$_{1-4}$)alkyl, halogeno-(C$_{2-4}$)alkoxy, hydroxy-(C$_{2-4}$)alkoxy, (C$_{2-4}$)alkanoyloxy-(C$_{2-4}$)alkoxy, (C$_{1-4}$)alkoxy-(C$_{2-4}$)alkoxy, carboxy-(C$_{1-4}$)alkoxy, (C$_{1-4}$)alkoxycarbonyl-(C$_{1-4}$)alkoxy, carbamoyl-(C$_{1-4}$)alkoxy, N-(C$_{1-4}$) alkylcarbamoyl-(C$_{1-4}$)alkoxy, N, N-di-[(C$_{1-4}$)alkyl]carbamoyl-(C$_{1-4}$)alkoxy, amino-(C$_{2-4}$)alkoxy, (C$_{1-4}$)alkylamino-(C$_{2-4}$)alkoxy, di-[(C$_{1-4}$)alkyl]amino-(C$_{2-4}$)alkoxy, (C$_{2-4}$)alkanoyloxy, hydroxy-(C$_{2-4}$)alkanoyloxy, (C$_{1-4}$)alkoxy-(C$_{2-4}$)alkanoyloxy, phenyl-(C$_{1-4}$)alkoxy, phenoxy-(C$_{2-4}$)alkoxy, anilino-(C$_{2-4}$)alkoxy, phenylthio-(C$_{2-4}$)alkoxy, piperidino-(C$_{2-4}$)alkoxy, morpholino-(C$_{2-4}$)alkoxy, piperazin-1-yl-(C$_{2-4}$)alkoxy, 4-(C$_{1-4}$)alkylpiperazin-1-yl-(C$_{2-4}$)alkoxy, halogeno-(C$_{2-4}$)alkylamino, hydroxy-(C$_{2-4}$)alkylamino, (C$_{2-4}$)alkanoyloxy-(C$_{2-4}$)alkylamino, (C$_{1-4}$)alkoxy-(C$_{2-4}$)alkylamino, carboxy-(C$_{1-4}$)alkylamino, (C$_{1-4}$)alkoxycarbonyl-(C$_{1-4}$)alkylamino, carbamoyl-(C$_{1-4}$)alkylamino, N-(C$_{1-4}$)alkylcarbamoyl-(C$_{1-4}$)alkylamino, N, N-di-[(C$_{1-4}$)alkyl]carbamoyl-(C$_{1-4}$)alkylamino, amino-(C$_{2-4}$)alkylamino, (C$_{1-4}$)alkylamino-(C$_{2-4}$)alkylamino, di-1(C$_{1-4}$)alkyl]amino-(C$_{2-4}$)alkylamino, phenyl-(C$_{1-4}$)alkylamino, phenoxy-(C$_{2-4}$)alkylamino, anilino-(C$_{2-4}$)alkylamino, phenylthio-(C$_{2-4}$)alkylamino, (C$_{2-4}$)alkanoylamino, (C$_{1-4}$)alkoxycarbonylamino, (C$_{1-4}$)alkylsulphonylamino, benzamido, benzenesulphonamido, 3-phenylureido, 2-oxopyrrolidin-1-yl, 2,5-dioxopyrrolidin-1-yl, halogeno-(C$_{2-4}$)alkanoylamino, hydroxy-(C$_{2-4}$)alkanoylamino, (C$_{1-4}$)alkoxy-(C$_{2-4}$)alkanoylamino, carboxy-(C$_{2-4}$)alkanoylamino, (C$_{1-4}$)alkoxycarbonyl-(C$_{2-4}$)alkanoylamino, carbamoyl-(C$_{2-4}$)alkanoylamino, N-(C$_{1-4}$)alkylcarbamoyl-(C$_{2-4}$)alkanoylamino, N,N-di-[(C$_1$-4)alkyl]carbamoyl-(C$_{2-4}$)alkanoylamino, amino-(C$_{2-4}$)alkanoylamino, (C$_{1-4}$)alkylamino-(C$_{2-4}$)alkanoylamino or di-[(C$_{1-4}$)alkyl]amino-(C$_{2-4}$)alkanoylamino;

the subclasses in which one of R$^U$ and R$^L$ is: (C$_{1-4}$)alkoxy; di-(C$_{1-4}$)alkylamino-(C$_{2-4}$)alkoxy, pyrrolidin-1-yl-(C$_{2-4}$)alkoxy, piperidino-(C$_{2-4}$)alkoxy, morpholino-(C$_{2-4}$)alkoxy, piperazin-1-yl-(C$_{2-4}$)alkoxy, 4-(C$_{1-4}$)alkylpiperazin-1-yl-(C$_{2-4}$)alkoxy, imidazol-1-yl-(C$_{2-4}$)alkoxy, di-(C$_{1-4}$)alkoxy-(C$_{2-4}$)alkylamino-(C$_{2-4}$)alkoxy, thiamorpholino-(C$_{2-4}$)alkoxy, 1-oxothiamorpholino-(C$_{2-4}$)alkoxy or 1,1-dioxothiamorpholino-(C$_{2-4}$)alkoxy, each independently optionally substituted with an —OH;

the subclasses in which one of R$^U$ and R$^L$ is OR$^J$, wherein R$^J$ is an alkyl or alkenyl moiety optionally further substituted with a hydroxy or alkoxy group, substituted or unsubstituted amino, cycloalkyl or heterocycloalkyl group;

the subclasses in which one of R$^U$ and R$^L$ is NH(CO)R$^J$;

the subclasses in which one of R$^U$ and R$^L$ is —O(M$_X$)R$^N$, wherein R$^N$ is hydrogen or a hydroxy or substituted or unsubstituted alkoxy group, substituted or unsubstituted amino, or a substituted or unsubstituted cycloalkyl or heterocycloalkyl group;

the subclasses in which one of R$^U$ and R$^L$ is —O(M$_{X'}$)R$^{N1}$, wherein R$^{N1}$ is hydroxyl, or substituted or unsubstituted methoxy, ethoxy, propoxy, pyrrolidinyl, piperidino, morpholino, piperazinyl, imidazolyl, thiamorpholino, oxothiamorpholino, or dioxothiamorpholino;

the subclasses in which R$^U$ is NR$^K$—CO—R$^M$, or NR$^K$—S(O)$_2$—R$^M$, wherein R$^K$ is hydrogen or a lower alkyl group and R$^M$ is hydrogen, lower alkyl, or —CR$^P$=CH(R$^Q$), wherein R$^P$ is hydrogen, halogen or C$_{1-6}$ alkyl and R$^Q$ is hydrogen, halogen, C$_{1-6}$perfluroalkyl, 1,1-difluoro(C$_{1-6}$)alkyl, C$_{1-6}$alkyl, —(CH$_2$)$_r$N-piperidinyl, —(CH$_2$)$_r$piperazinyl, —(CH$_2$)$_r$pyrrolidyl, —(CH$_2$)$_r$pyridinyl, —(CH$_2$)$_r$N-imidazolyl, —(CH$_2$)$_r$—N-morpholino, —(CH$_2$)$_r$—N-thiomorpholino, —CH=CH$_2$, —(CH=CH—(C$_{1-6}$alkyl), —(CH$_2$)$_r$—N-hexahydroazepine, —(CH$_2$)$_r$N(C$_{1-6}$alkyl)$_2$, 1-oxo-C$_{1-6}$alkyl, carboxy, (C$_{1-6}$)alkyloxycarbonyl, N-(C$_{1-6}$)alkylcarbamoyl, phenyl or substituted phenyl, and r is 1, 2, 3 or 4;

the subclasses in which R$^L$ is —O(CH$_2$)$_r$morpholino, wherein r is 1, 2, 3 or 4;

the subclasses in which R$^U$ is (C$_{1-4}$)alkoxy; di-(C$_{1-4}$)alkylamino-(C$_{2-4}$)alkoxy, pyrrolidin-1-yl-(C$_{2-4}$)alkoxy, piperidino-(C$_{2-4}$)alkoxy, morpholino-(C$_{2-4}$)alkoxy, piperazin-1-yl-(C$_{2-4}$)alkoxy, 4-(C$_{1-4}$)alkylpiperazin-1-yl-(C$_{2-4}$)alkoxy, imidazol-1-yl-(C$_{2-4}$)alkoxy, di-(C$_{1-4}$)alkoxy-(C$_{2-4}$)alkylamino-(C$_{2-4}$)alkoxy, thiamorpholino-(C$_{2-4}$)alkoxy, 1-oxothiamorpholino-(C$_{2-4}$)alkoxy or 1,1-dioxothiamorpholino-(C$_{2-4}$)alkoxy, each independently optionally substituted with a hydroxy group;

the subclasses in which R$^U$ is 2-dimethylaminoethoxy, 2-diethylaminoethoxy, 3-dimethylaminopropoxy, 3-diethylaminopropoxy, 2-pyrrolidin-1-yl)ethoxy, 3-pyrolidin-1-yl)propoxy, 2-piperidinoethoxy, 3-piperidinopropoxy, 2-morpholinoethoxy, 3-morpholinopropoxy, 2(4-methylpiperazin-1-yl)ethoxy, 2-imidazol-1-yl)ethoxy, 3-imidazol-1-yl)propoxy, 2-[di-2-methoxyethyl)amino]ethoxy, or 3-morpholino-2-hydroxypropoxy;

the subclasses in which R$^U$ is 3-dimethylaminopropoxy, 3-diethylaminopropoxy, 3-(pyrrolidin-1-yl)propoxy, 3-morpholinopropoxy, or 3-morpholino-2-hydroxypropoxy;

Compounds of particular interest further include, among others, those which share the attributes of one or more of the foregoing subclasses, i.e., which contain an R$^U$ or R$^L$ moiety of one subclass, a moiety J of another cubclass and a moiety R$^B$ of another subclass.

Some of those subclasses are illustrated by the following sorts of compounds, which are of particular interest:

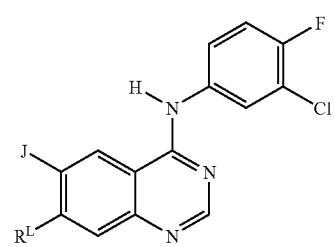

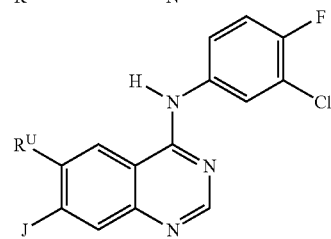

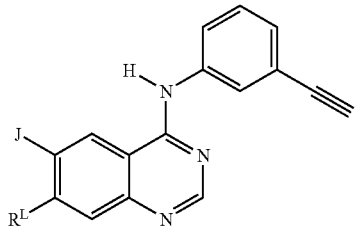

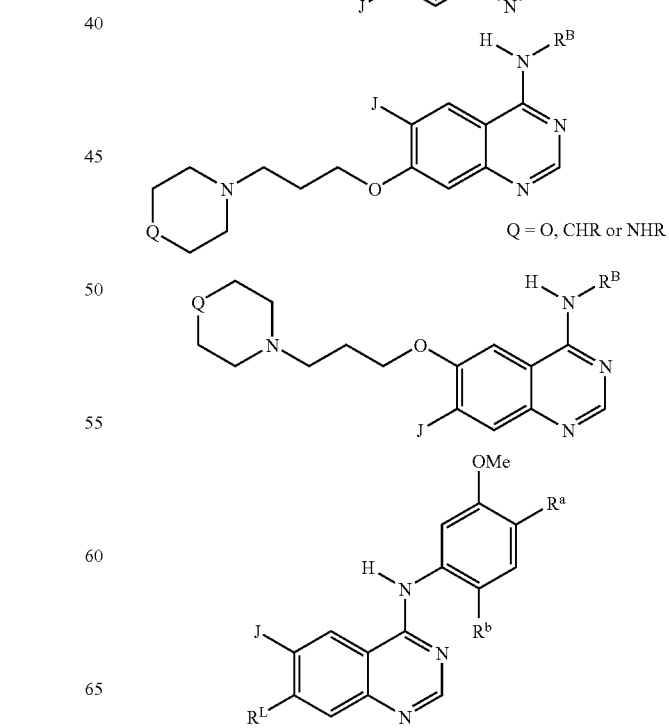

-continued

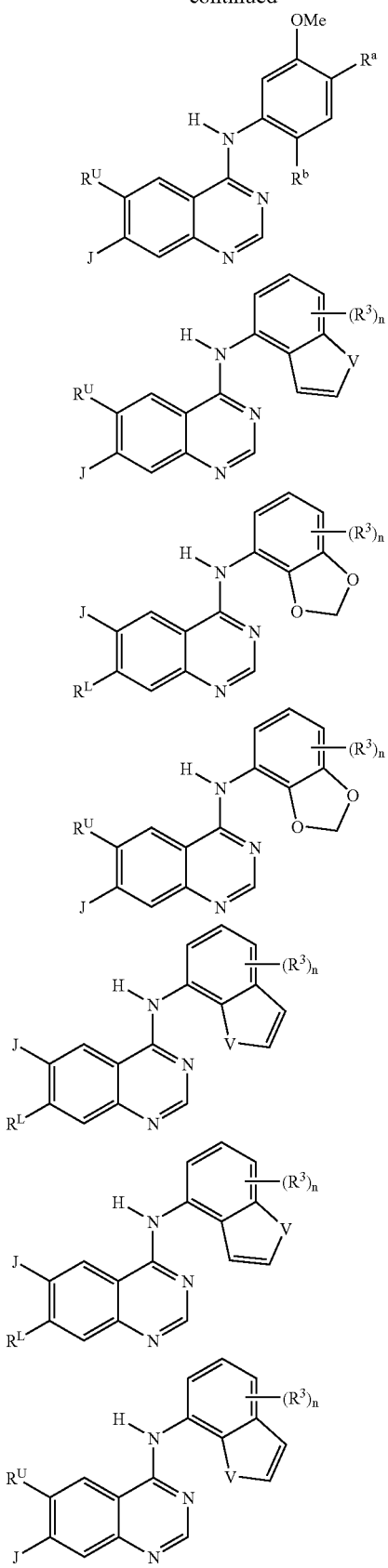

Of particular interest are the subsets of compounds of Formulas I, I-A and I-B, and of each of the various classes, subclasses and general formula s note d herein, including among others the eighteen structures shown just above, wherein J is —PO(Me)$_2$, wherein J is —PO(Et)$_2$, wherein J is —PO(propyl)$_2$, wherein J is —PO(OEt)(Me), wherein J is —PO(Me)$_2$, and wherein J is —PO(OEt)$_2$, respectively.

3. Compounds and Definitions

This invention provides a new family of compounds with a range of biological properties. Compounds of this invention have biological activities relevant for the treatment of diseases including bone related disorders, disorders related to cellular proliferation (e.g., various forms of cancer), rheumatoid arthritis, osteoporosis and other diseases involving untoward bone resorption (e.g., Paget's Disease, primary and secondary hyperparathyroidism, humoral hypercalcemia of malignancy, and various cancers where bone resorption is increased), restenosis following coronary angioplasty, glomerulonephritis, glomerulosclerosis, liver cirrhosis, pulmonary fibrosis, disorders involving increased vascular permeability and/or angiogenesis and others. More generally, the compounds are useful in the regulation of signal transduction pathways. For example, certain compounds of the invention are useful for inhibiting tyrosine kinases, including without limitation receptor-type tyrosine kinases such as those of the HER (e.g. EGFR, HER2, HER3 and HER4), PDGF and FLK families (including, e.g., VEGF-R1 and VEGF-R2) as well as non-receptor-type tyrosine kinases such as those of the Src and abl subfamilies, again as non-imiting examples.

Compounds of this invention include those described or illustrated in part by the various classes, subclasses and species disclosed herein.

Some of the compounds contain one or more asymmetric centers. This invention encompasses those compounds as an individual enantiomer or diastereomer or as a mixture of enantiomers or diastereomers. In certain embodiments, the compounds of the invention are in the form of a single enantiomer or diastereomer, substantially free from other enantiomers or diastereomers (i.e., in a form containing less than 10%, preferably less than 5% and in some cases even more preferably less than 1% of one or more other enantiomers or diasteriomers, by weight or molarity. In certain other embodiments, a mixture of stereoisomers or diastereomers is provided. In addition, compounds of this invention may contain one or more heavy, less common and/or readily detectable isotopes, e.g. deuterium in place of one or more hydrogen atoms, N15 in place of one or more N14 atoms, etc. Such isotope design choices can be useful for a variety of purposes, including among others, determining tissue distribution or the rate or mechanism of biological clearance, or for changing the rate of metabolism or clearance, of the compound.

Additionally, this invention provides pharmaceutically acceptable derivatives of our compounds, and methods of treating a subject using these compounds, pharmaceutical compositions containing one or more of the compounds or a pharmaceutically acceptable derivative thereof, or either of these in combination with one or more additional therapeutic agents. The phrase, "pharmaceutically acceptable derivative", as used herein, denotes any pharmaceutically acceptable salt, ester, or salt of such ester, of such compound, or any other adduct or derivative which, upon administration to a patient, is capable of providing (directly or indirectly) a compound as otherwise described herein, or a metabolite or residue thereof. Pharmaceutically acceptable derivatives thus include among others pro-drugs. A pro-drug is a derivative of a compound, often with significantly reduced pharmacological activity, which contains an additional moiety which is susceptible to removal in vivo yielding the parent molecule-as the pharmacologically active species. An example of a pro-drug is an ester which is cleaved in vivo to yield a compound of interest. Pro-drugs of a variety of compounds, and materials and methods for derivatizing the parent compounds to create the pro-drugs, are known and may be adapted to the present invention. Certain exemplary pharmaceutical compositions and pharmaceutically acceptable derivatives will be discussed in more detail herein below.

Illustrative compounds and a number of important definitions are described in more detail below. For purposes of this document, the chemical elements are identified in accordance with the Periodic Table of the Elements, CAS version, Handbook of Chemistry and Physics, 75$^{th}$ Ed., inside cover, and specific functional groups are generally defined as described therein. Additionally, general principles of organic chemistry, as well as specific functional moieties and reactivity, are described in "Organic Chemistry", Thomas Sorrell, University Science Books, Sausalito: 1999. Furthermore, it will be appreciated by one of ordinary skill in this art that the synthetic methods, as described herein, can utilize a variety of protecting groups. The term "protecting group" denotes a moiety which can be used to temporarily block a particular functional group in a multifunctional compound (e.g., to temporarily block a —OH, —NH—, —SH, —CHO, —COOH, —C=O—, —P(=O)(OH)—, etc.) so that a reaction can be carried out selectively at another reactive site, after which the protecting group may be removed. In preferred cases, a protecting group reacts selectively in good yield to give a protected derivative in which the otherwise reactive site is "blocked", i.e. is stable to the reagents and conditions to be used in a chemical transformation elsewhere in the molecule. The protecting group is preferably selectively removable in practicable yield without unintended loss of other functional groups of the protected molecule; forms a separable derivative (more preferably without the generation of new stereogenic centers); and has a minimum of additional functionality to avoid further sites of reaction. A wide variety of methods and materials are known to the practitioner for temporparily protecting otherwise reactive sites in a compound while a chemical transformation is effected elsewhere in the molecule. One of many reference works describing such protecting groups is "Protective Groups in Organic Synthesis" Third Ed. Greene, T. W. and Wuts, P. G., Eds., John Wiley & Sons, New York: 1999. For additional background information on protecting group methodologies (materials, methods and strategies for protection and deprotection) and other synthetic chemistry transformations useful in producing the compounds described herein, see in R. Larock, Comprehensive organic Transformations, VCH Publishers (1989); L. Fieser and M. Fieser, Fieser and Fiesers Reagents for Organic Synthesis, John Wiley and Sons (1994); and L. Paquette, ed., Encyclopedia of Reagents for Organic Synthesis, John Wiley and Sons (1995).

As described herein, our compounds may contain one or more of a variety of substituents, such as are illustrated in connection with particular classes, subclasses and species of the invention. In general, the term "substituted" and "substituent", whether preceded by the term "optionally" or not, refer to the replacement of hydrogen radicals in a given structure with the radical of a specified substituent. When more than one position of a compound may each contain a substituent selected from a group of possible substituents, the substituents at those sites may be the same or different at every position. Combinations of substituents and variables are preferably those that result in the formation of stable compounds. The term "stable", as used herein, refers to compounds that possess stability sufficient to allow their production and detection and preferably their recovery, purification and use for one or more of the purposes disclosed herein.

The term "aliphatic", as used herein, includes both saturated and unsaturated, straight chain (i.e., unbranched), branched, cyclic, or polycyclic aliphatic hydrocarbons, which are optionally substituted with one or more functional groups. The term includes, but is not limited to, alkyl, alkenyl, alkynyl, cycloalkyl, cycloalkenyl, and cycloalkynyl moieties. Thus, as used herein, the term "alkyl" includes straight, branched and cyclic alkyl groups. An analogous convention applies to other generic terms such as "alkenyl", "alkynyl" and the like. Furthermore, as used herein, the terms "alkyl", "alkenyl", "alkynyl" and the like encompass both substituted and unsubstituted groups. The term "lower" as applied to alkyl or other aliphatic groups indicates a group having 1–6 carbon atoms (which may be substituted or unsubstituted as specified). Size ranges may be denoted in this document using common conventions, cinluding speciflying the numerical range of carbon atoms before the word, "Carbon" or "C" or as a subscript thereto. For instance, an aliphatic group having 1–6 carbon atoms may be designated a "1–6C" or "$C_{1-6}$" aliphatic group.

Unless otherwise specified, the alkyl, alkenyl and alkynyl groups contain 1–20 aliphatic carbon atoms. In some embodiments, they contain 1–10 aliphatic carbon atoms. In other embodiments, they contain 1–8 aliphatic carbon atoms. In still other embodiments, they contain 1–6 aliphatic carbon atoms, and in yet other embodiments, 1–4 carbon atoms. Illustrative aliphatic groups thus include, but are not limited to, for example, methyl, ethyl,allyl, n-propyl, isopropyl, cyclopropyl, —CH$_2$-cyclopropyl, methallyl, n-butyl, sec-butyl, isobutyl, tert-butyl, cyclobutyl, —CH$_2$-cyclobutyl, n-pentyl, sec-pentyl, isopentyl, tert-pentyl, cyclopentyl, —CH$_2$-cyclopentyl, n-hexyl, sec-hexyl, cyclohexyl, —CH$_2$-cyclohexyl moieties and the like, which again, may bear one or more substituents. Benzyl, phenethyl, heteroaromatic analogs, and substituted derivatives of such moieties are thus considered substituted aliphatic moieties. Alkenyl groups include, but are not limited to, for example, ethenyl, propenyl, butenyl, 1-methyl-2-buten-1-yl, and the like. Representative alkynyl groups include, but are not limited to, ethynyl, 2-propynyl (propargyl), 1-propynyl and the like.

The terms "alkoxy" and "thioalkyl" as used herein refer to an alkyl group, as previously defined, attached to the parent molecular moiety through an oxygen atom or through a sulfur atom. Examples of alkoxy, include but are not limited to, methoxy, ethoxy, propoxy, isopropoxy, n-butoxy, tert-butoxy, neopentoxy and n-hexoxy. Examples of thioalkyl include, but are not limited to, methylthio, ethylthio, propylthio, isopropylthio, n-butylthio, and the like.

The term "alkylamino" refers to a group having the structure —NHR' wherein R' is alkyl, as defined herein. Examples of alkylamino include, but are not limited to, methylamino, ethylamino, iso-propylamino and the like. In certain embodiments, $C_1$–$C_3$ alkylamino groups are utilized in the present invention.

Some examples of substituents for various optionally substituted moieties of compounds of the invention include, but are not limited to aliphatic; heteroaliphatic; aryl; heteroaryl; alkoxy; aryloxy; heteroalkoxy; heteroaryloxy; alkylthio; arylthio; heteroalkylthio; heteroarylthio; F; Cl; Br; I; —OR$_x$; —NO$_2$; —CN; —CF$_3$; —CH$_2$CF$_3$; —CHCl$_2$; —CH$_2$OH; —CH$_2$CH$_2$OH; —CH$_2$NH$_2$; —CH$_2$SO$_2$CH$_3$; —C(O)R$_x$; —CO$_2$(R$_x$); —CON(R$_x$)$_2$; —OC(O)R$_x$; —OCO$_2$R$_x$; —OCON(R$_x$)$_2$; —N(R$_x$)$_2$; —S(O)$_2$R$_x$; —SO$_2$NR$_{x2}$; and —NR$_x$ (CO)R$_x$ moieties—wherein each occurrence of R$_x$ is a group independently chosen from: H; an aliphatic or heteroaliphatic moiety which may be substituted or unsubstituted, branched or unbranched, cyclic or acyclic; and an optionally substituted aryl or heteroaryl moiety. In addition, substituents include phosphorus-containing moieties, as defined herein including the various illustrative phosphorus-containing moieties. Additional examples of generally applicable substituents are illustrated by the specific embodiments depicted in this docment, including but not limited to those shown in the Examples that are described herein. The foregoing is intended to be encompassed by references to "substituents" and "substituted" as those terms are used in this document.

The terms "aryl" and "heteroaryl", as used herein, refer to stable mono- or polycyclic, heterocyclic, polycyclic, and polyheterocyclic unsaturated moieties having preferably 3–14 carbon atoms, each of which may be substituted or unsubstituted. Substituents include any of the previously mentioned substituents. Non-limiting examples of useful aryl ring groups include phenyl, halophenyl, alkoxyphenyl, dialkoxyphenyl, trialkoxyphenyl, alkylenedioxyphenyl, naphthyl, phenanthryl, anthryl, phenanthro and the like. Examples of typical heteroaryl rings include 5-membered monocyclic ring groups such as thienyl, pyrrolyl, imidazolyl, pyrazolyl, furyl, isothiazolyl, furazanyl, isoxazolyl, thiazolyl and the like; 6-membered monocyclic groups such as pyridyl, pyrazinyl, pyrimidinyl, pyridazinyl, triazinyl and the like; and polycyclic heterocyclic ring groups such as benzo[b]thienyl, naphtho[2,3-b]thienyl, thianthrenyl, isobenzofuranyl, chromenyl, xanthenyl, phenoxathienyl, indolizinyl, isoindolyl, indolyl, indazolyl, purinyl, isoquinolyl, quinolyl, phthalazinyl, naphthyridinyl, quinoxalinyl, quinazolinyl, benzothiazole, benzimidazole, tetrahydroquinoline cinnolinyl, pteridinyl, carbazolyl, beta-carbolinyl, phenanthridinyl, acridinyl, perimidinyl, phenanthrolinyl, phenazinyl, isothiazolyl, phenothiazinyl, phenoxazinyl, and the like (see e.g. Katritzky, Handbook of Heterocyclic Chemistry). The aryl or heteroaryl moieties may be substituted with one to five members selected from the group consisting of hydroxy, C1–C8 alkoxy, C1–C8 branched or straight-chain alkyl, acyloxy, carbamoyl, amino, N-acylamino, nitro, halo, trihalomethyl, cyano, and carboxyl. Aryl moieties thus include, by way of example and not limiatation, phenyl; substituted phenyl bearing one or more substituents selected from groups including: halo such as chloro or fluoro, hydroxy, C1–C6 alkyl, acyl, acyloxy, C1–C6 alkoxy (such as methoxy or ethoxy, including among others dialkoxyphenyl moieties such as 2,3-, 2,4-, 2,5-, 3,4- or 3,5-dimethoxy or diethoxy phenyl or such as methylenedioxyphenyl, or 3-methoxy-5-ethoxyphenyl; or trisubstituted phenyl, such as trialkoxy (e.g., 3,4,5-trimethoxy or ethoxyphenyl), 3,5-dimethoxy-4-chloro-phenyl, etc.), amino, —SO$_2$NH$_2$, —SO$_2$NH(aliphatic), —SO$_2$N(aliphatic)$_2$, —O-aliphatic-COOH, and —O-aliphatic-NH$_2$ (which may contain one or two N-aliphatic or N-acyl substituents).

The aryl and heteroaryl moieties may be attached to an alkyl or heteroalkyl moiety to form -(alkyl)aryl, -(heteroalkyl)aryl, -(heteroalkyl)aryl, and -(heteroalkyl)heteroaryl moieties. Moieties such as -alkyl)aryl, -heteroalkyl)aryl, -(heteroalkyl)aryl, and -(heteroalkyl)heteroaryl" may be considered "substituted aliphatic" and "substituted heteroaliphatic" groups, respectively and are included within the definitions of these terms. Substituents for exemplary aryl and heteroaryl moieties include, but are not limited to, any of the substitutents previously mentioned or alluded to.

It will be appreciated that aryl and heteroaryl groups can be unsubstituted or substituted, wherein substitution includes replacement of one or more (e.g. 1, 2 or 3) of the hydrogen atoms thereon with substituents such as are described herein or illustrated in any of the illustrative examples herein.

The term "cycloalkyl", as used herein, refers specifically to groups having three to ten, preferably three to seven carbon atoms. Suitable cycloalkyls include, but are not limited to cyclopropyl, cyclobutyl, cyclopentyl, cyclohexyl, cycloheptyl and the like, which, as in the case of other aliphatic, heteroaliphatic or hetercyclic moieties, may optionally be substituted as previously described.

The term "heteroaliphatic", as used herein, refers to aliphatic moieties which contain one or more oxygen, sulfur, nitrogen, phosphorous or silicon atoms, e.g., in place of carbon atoms. Heteroaliphatic moieties may be substituted or unsubstituted, branched, unbranched, cyclic or acyclic, and include saturated and unsaturated heterocycles such as morpholino, pyrrolidinyl, etc.

The terms "halo" and "halogen" as used herein refer to an atom selected from fluorine, chlorine, bromine and iodine.

The term "haloalkyl" denotes an alkyl group, as defined above, having one, two, or three halogen atoms attached thereto and is exemplified by such groups as chloromethyl, bromoethyl, trifluoromethyl, and the like.

The term "heterocycloalkyl" or "heterocycle", as used herein, refers to a non-aromatic 5-, 6- or 7-membered ring or a polycyclic group, including, but not limited to a bi- or tricyclic group, having one to four heteroatoms independently chosen from oxygen, sulfur and nitrogen, wherein (i) each 5-membered ring has 0 to 1 double bonds and each 6-membered. ring has 0 to 2 double bonds, (ii) the nitrogen and sulfur heteroatoms may be optionally be oxidized, (iii) the nitrogen heteroatom may optionally be quaternized, and (iv) any of the above heterocyclic rings may be fused to a benzene ring. Representative heterocycles include, but are not limited to, pyrrolidinyl, pyrazolinyl, pyrazolidinyl, imidazolinyl, imidazolidinyl, piperidinyl, piperazinyl, oxazolidinyl, isoxazolidinyl, morpholinyl, thiazolidinyl, isothiazolidinyl, and tetrahydrofuryl. The heterocyclic moiety may be substituted or unsubstituted.

As used herein, the phrase, "phosphorus-containing moiety" includes, but is not limited to, phosphites, phosphonites, phosphenites, phosphines, phosphates, phosphonates, phosphenates, phosphine oxides, bisphosphonates, thiophosphates, thiophosphonates, thiophosphenates, thiophosphine oxides, mono- or (where permitted) di- or tri- amides and esters of any of the foregoing as well as the phosphorus-containing moieties disclosed or otherwise described herein, including in the accompanying text and illustrative classes, subclasses, and species of compounds disclosed herein.

4. Synthetic Overview

The practitioner has a well-established literature of quinazoline chemistry to draw upon, in combination with the information contained herein, for guidance on synthetic strategies, protecting groups, and other materials and methods useful for the synthesis of the compounds of this invention, including compounds containing the various $R^B$, $R^U$ and $R^L$ substituents. Naturally, the examples and illustrations may be readily adapted to the preparation of many other compounds analogous to those depicted here.

The various patent documents and other references cited herein provide helpful background information on producing variously analogously substituted quinazolines or relevant intermediates, as well as information on formulation, uses, and administration of prior quinazolines which may be of interest. See e.g. Bridges, 2001, Chem. Rev., 101: 2541–2571; Barker et al, 2001, Bioorganic & Medicinal Chemistry Letters 11: 1911–1914; Boschelli, 2002, Current Topics in medicinal Chemistry, 2:1051–1063; Boschelli et al, 2001, J. Med. Chem. 44: 822–833; Adjel, 2001, Drugs of the future, 26(11): 1087–1092; Matsuno et al, 2002, J. Med. Chem. 45: 4513–4523; Anderson et al, 2001, Int. J. Cancer, 94: 774–782; U.S. Pat. No. 6,423,716; and WO 02/16351; and references cited in all of the foregoing. Additional references of interest include: WO 00230924; WO 00230926; WO 00234744; WO 02085895; WO 02092577; WO 02092578; WO 02092579; WO 0279122; WO 00216352; WO 03055866; U.S. Pat. Nos. 5,747,498; 5,457, 105; 5,616,582; 6,344,459; WO 97/22596; WO 97/30035; WO 97/32856; WO 97/38994; WO 98/13354; WO 00/20402; WO 96/15118; WO 00/51991; WO 00/55141; EP 520 722, EP 602 851; EP 566 226; EP 635 498, EP 635 507, EP 1044969; EP 0837063; WO 96/30347; WO 96/33980; and WO 99/55683, as well as the following: WO0216351A1, WO0147890A1, U.S. Pat. Nos. 6,495,556, 6,495,353, 6,469,013, 6,388,063, 6,362,336, 6,358,962, 6,342,593, 6,337,335, 6,316,454, 6,313,129, 6,297,264, 6,291,455, 6,258,951, 6,258,820, 6,245,774, 6,239,161, 6,235,746, 6,228,641, 6,207,401, 6184225, 6,133,257, 6,114,333, 6,103,728, 6,093,716, 6,090,838, 6,077,854, 6,071,921, 6,057,329, 6,057,320, 6,048,866, 6,015,814, 6,002,008, 5,981,569, 5,962,492, 5,962,483, 5,962,458, 5,958,935, 5,955,464, 5,952,333, 5,942,514, 5,932,574, 5,922,741, 5,914,343, 5,866,593, 5,866,572, 5,837,815, 5,837,524, 5,821,246, 5,814,630, 5,804,396, 5,792,771, 5,770,603, 5,770,599, 5,763,441 and 5710158.

Additionally, as detailed in the specification, a variety of phosphorus-containing moieties are utilized in the design and synthesis of the compounds of the invention. In addition to the phosphorus-containing moieties as described above and in U.S. Pat. Nos. 6,482852 and 6,420,384 and in WO 01/44258, WO 01/44259, and WO 01/44260, certain other phosphorus-containing moieties, such as the described dialkyl phenyl phosphine oxide compounds can be synthesized according to the procedures and schemes outlined herein.

For instance, by adapting conventional materials and methods for the assembly of substituted quinazolines, but using intermediates or additional reagents such as are disclosed herein, one may prepare compounds of this invention as illustrated in the following synthetic approaches (recognizing that many other approaches and variations will be apparent to the practitioner, are within the scope of this invention, and should be considered):

As should be clear from the references noted above, there are a variety of ways available to the practitioner for assembling substituted quinazolines. One approach for the production of quinazolines of Formula I is illustrated below.

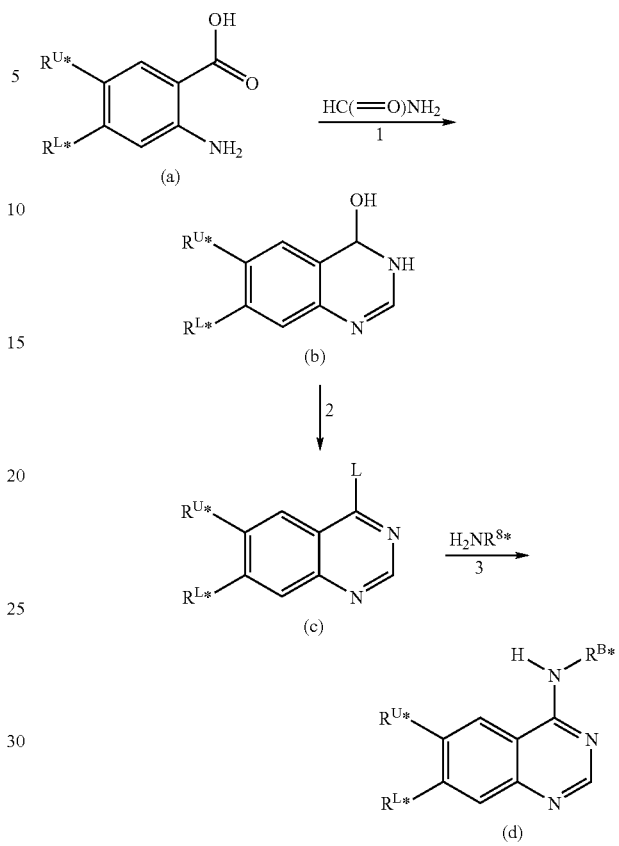

In that approach, a quinazoline (c) is prepared which contains at position 4 a displaceable group, L, and typically the desired substituents $R^U$ and $R^L$ as well, or protected or precursor forms of one or both of them (indicated by the asterisk). That reactive quinazoline (c) is reacted with an aryl or heteroaryl amine, $H_2NR^{B*}$, which comprises the desired RB moiety, or again, a protected or precursor form thereof, as indicated by the asterisk.

Such reactions are often carried out in the presence of a suitable acid or base. Illustrative suitable acids include, e.g., an inorganic acid such as HCl or HBr. Examples of suitable bases include organic amine bases (such as pyridine, 2,6-lutidine, collidine, 4-dimethylaminopyridine, triethylamine, morpholine, N-methylmorpholine or diazabicyclo[5.4.0]undec-7-ene) and alkali or alkaline earth metal carbonates or hydroxides, for example sodium carbonate, potassium carbonate, calcium carbonate, sodium hydroxide or potassium hydroxide, or, an alkali metal hydride such as sodium hydride, or an alkali metal amide such as sodium amide or sodium 1,1,1,3,3,3-hexamethyidisilazide.

Illustrative displaceable groups L include, e.g., a halogen, alkoxy, aryloxy or sulphonyloxy group (e.g., a chloro, bromo, methoxy, phenoxy, pentafluorophenoxy, methanesulphonyloxy or toluene sulphonyloxy group). Such displacements are often carried out in an inert solvent or diluent, e.g., an alcohol or ester such as methanol, ethanol, isopropanol or ethyl acetate; a halogenated solvent such as methylene chloride, chloroform or carbon tetrachloride; an ether such as tetrahydrofuran or 1,4-dioxan; an aromatic solvent such as toluene; or a dipolar aprotic solvent such as N,Nmdimethylfom-lamide, N N-dimethylacetamide, N-methylpyrrolidin-2-one or dimethylsulphoxide. The reactions are commonly carried out at a temperature ranging from about 10 to 250° C., typically in the range 40 to 120° C.

Typically, the quinazoline (c) is reacted with the aryl or heteroaryl amine in the presence of a protic solvent such as isopropanol, often in the presence of an acid such as hydrogen chloride gas in diethyl ether, and at a temperature in the range, for example, 25 to 150° C., often at or near the reflux temperature of the reaction solvent.

The quinazoline (d) may be obtained from this process as the free base or as a salt with the acid of the formula H-L. To obtain the free base from the salt, the salt may be treated with a suitable base, for example, an organic amine base such as, for example, pyridine, 2,6-lutidine, collidine, 4-dimethylaminopyridine, triethylamine, morpholine, N-methylmorpholine or diazabicyclo[5.4.0]undec-7-ene, or, for example, an alkali or alkaline earth metal carbonate or hydroxide, for example sodium carbonate, potassium carbonate, calcium carbonate, sodium hydroxide or potassium hydroxide.

Protecting groups may generally be chosen from the many different types described in the scientific and patent literature or otherwise known to the skilled chemist as appropriate for protecting the functionality in question. The protecting groups may be introduced and in due course removed using conventional methods and materials.

A non-limiting list of illustrative methods and materials for protection and deprotection is presented below.

A carboxy group may be protected in the form of an aliphatic, arylaliphatic or silyl ester. Examples of carboxy protecting groups include straight or branched chain (1–12C)alkyl groups (e.g., isopropyl, and tert-butyl); lower alkoxy- lower alkyl groups (e.g., methoxymethyl, ethoxymethyl and isobutoxymethyl); lower acyloxy-lower alkyl groups, (e.g., acetoxymethyl, propionyloxymethyl, butyryloxymethyl and pivaloyloxymethyl); lower alkoxycarbonyloxy-lower alkyl groups (e.g., 1-methoxycarbonyloxyethyl and 1-ethoxycarbonyloxyethyl); aryl-lower alkyl groups (e.g., benzyl, 4-methoxybenzyl, 2-nitrobenzyl, 4-nitrobenzyl, benzhydryl and phthalidyl); tri(lower alkyl)silyl groups (e.g., trimethylsilyl and tert-butyldimethylsilyl); tri(lower alkyl)silyl-lower alkyl groups (e.g., trimethylsilylethyl); and (2–6C)alkenyl groups (e.g., allyl). Methods particularly appropriate for the removal of carboxyl protecting groups include for example acid-, base-, metal- or enzymically-catalysed cleavage.

Hydroxy protecting groups include lower alkyl groups (e.g., tert-butyl), lower alkenyl groups (e.g., allyl); lower alkanoyl groups (e.g., acetyl); lower alkoxycarbonyl groups (for example tert-butoxycarbonyl); lower alkenyloxycarbonyl groups (e.g., allyloxycarbonyl); aryl-lower alkoxycarbonyl groups (e.g., benzyloxycarbonyl, 4-methoxybenzyloxy-carbonyl, 2-nitrobenzyloxycarbonyl and 4mnitrobenzyloxycarbonyl); tri(lower alkyl)silyl (for example trimethylsilyl and tert-butyldimethylsilyl) and aryl-lower alkyl (e.g., benzyl) groups.

Examples of amino protecting groups include formyl, aryl-lower alkyl groups (e.g., benzyl and substituted benzyl, 4-methoxybenzyl, 2-nitrobenzyl and 2,4-dimethoxybenzyl, and triphenylmethyl); di-4 manisylmethyl and furylmethyl groups; lower alkoxycarbonyl (e.g., tert-butoxycarbonyl); lower alkenyloxycarbonyl (e.g., allyloxycarbonyl); arylmlower alkoxycarbonyl groups (e.g., benzyloxycarbonyl, 4 mmethoxybenzyloxycarbonyl, 2-nitrobenzyloxycarbonyl and 4-nitrobenzyloxycarbonyl); trialkylsilyl (e.g., trimethylsilyl and tert-butyldimethylsilyl); alkylidene (e.g., methylidene) and benzylidene and substituted benzylidene groups.

Hydroxy and amino protecting groups may be removed by methods which include, e.g., acid-, base-, metal- or enzymically-catalyzed hydrolysis for groups such as 2-nitrobenzyloxycarbonyl, hydrogenation for groups such as benzyl and photolytically for groups such as 2-nitrobenzyloxycarbonyl.

Advanced Organic Chemistry, 4th Edition, by J. March, published by John Wiley & Sons 1992, provides general guidance on reaction conditions and reagents. Protective Groups in Organic Synthesis, 2d Edition, by T. Green et al., also published by John Wiley & Son, provides general guidance on protecting groups.

Quinazoline starting materials (c) may be obtained by conventional procedures. For example, a 3,4-dihydroquinazolin-4-one (b) (in which RU and/or RL is protected if necessary), may be reacted with a halogenating agent such as thionyl chloride, phosphoryl chloride or a mixture of carbon tetrachloride and triphenylphosphine, after which any protecting group that is present may be removed by conventional means (prior to or after condensations with the aryl or heteraryl amine).

The 4-chloroquinazoline so obtained may be converted, if required, into a 4-pentafluoro-phenoxyquinazoline by reaction with pentafluorophenol in the presence of a suitable base such as potassium carbonate and in the presence of a suitable solvent such as N,N-dimethylformamide.

A wide variety of suitable aryl and heteraryl amines, substituted as desired and with any appropriate protecting groups, may be obtained by conventional procedures, or are commercially available or in protected or unprotected forms. Among others, the following types of anilines are of particular interest for use in preparing compounds of this invention:

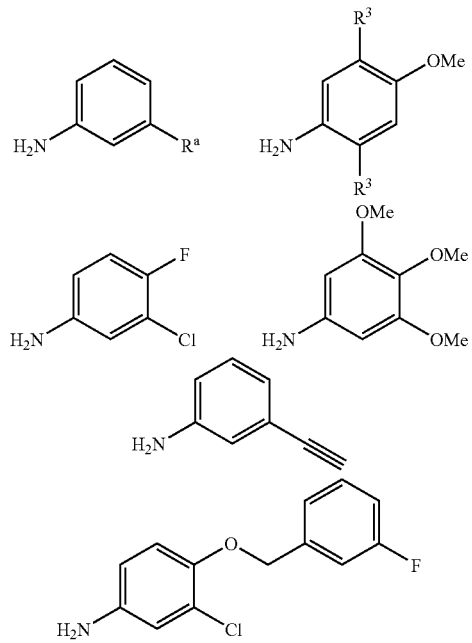

-continued

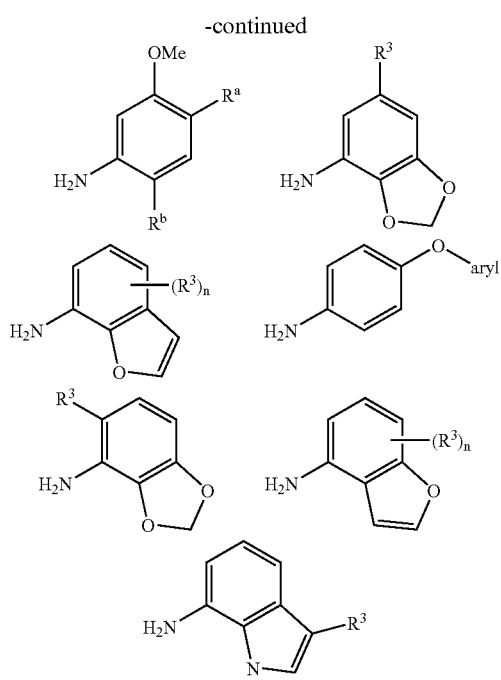

where $R^a$, $R^b$ and $R^3$ are as previously defined.

Assorted methods and materials are known in the art for attaching various arms, to quinazoline templates and may be adapted for use in preparing the compounds of this invention. Methods and materials for introducing various moieties, J, are illustrated in the examples below. The introduction of J and the introduction of $R^U$ and $R^L$ may be carried out in either order, and before or after the condensation with the aryl or heteroaryl amine, depending on the functional groups desired and with appropriate protection and deprotection. Thus, in the schematic above, $R^{U}*$ and $R^{L}*$ are the desired $R^U$ and $R^L$ substituents or protected or precursor forms thereof, where the protected or precursor forms may be modified before or after step 3 to generate the desired substituent $R^B$, $R^L$ and $R^U$ substituents. For example, $R^{U}*$ or $R^{L}*$ may comprise a hydroxyl group which subsequently is alkylated to form an aliphatic ether, or which is subsequently converted to a trifluoromethanesulfonic acid ester or other suitable leaving group and then converted to a desired phosphorus-containing moiety, J. In other cases, $R^{U}*$ or $R^{L}*$ may be an —OAc group which is replaced by a substituted or unsubstituted aliphatic ether. In other cases, $R^{U}*$ or $R^{L}*$ is a desired moiety, J, or a protected or precursor form thereof that may, depending on its nature, be converted into J before or after step 3.

To prepare a pharmaceutically-acceptable salt of a quinazoline of Formula I, an acid-addition salt for example may be obtained by reaction of the quinazoline with a suitable acid using a conventional procedure.

5. Uses, Formulations, Administration

Pharmaceutical Uses; Indications

This invention provides compounds having biological properties which make them of interest for treating or modulating disease in which kinases may be involved, symptoms of such disease, or the effect of other physiological events mediated by kinases. For instance, a number of compounds of this invention have been shown to inhibit tyrosine kinase activity of the Epidermal Growth Factor Receptor (EGF-R), among other tyrosine kinases which are believed to mediate the growth, development and/or metastasis of cancer. A number of compounds of the invention have also been found to possess potent inhibitory activity against the MDA-468 tumor cell line. Inhibitory potencies as powerful as that of Iressa have been observed in such assays.

Without wishing to be bound by any particular theory, it is known that the EGF family of receptor tyrosine kinases (and certain other receptor tyrosine kinases) are frequently present in common human cancers such as breast cancer (Sainsbury et. al., Brit. J. Cancer, 1988, 58, 458; Guerin et al., Oncogene Res., 1988, 3, 21 and Klijn et al., Breast Cancer Res. Treat., 1994, 29, 73), non-small cell lung cancers (NSCLCs) including adenocarcinomas (Cerny et al., Brit. J. Cancer, 1986, 54, 265; Reubi et al., Int. J. Cancer, 1990, 45, 269; and Rusch et al., Cancer Research, 1993, 53, 2379) and squamous cell cancer of the lung (Hendler et al., Cancer Cells, 1989, 7, 347), bladder cancer (Neal et. al., Lancet, 1985, 366), oesophageal cancer (Mukaida et al., Cancer, 1991, 68, 142), gastrointestinal cancer such as colon, rectal or stomach cancer (Bolen et al., Oncogene Res., 1987, 1, 149), cancer of the prostate (Visakorpi et al., Histochem. J., 1992, 24, 481), leukaemia (Konaka et al., Cell, 1984, 37, 1035) and ovarian, bronchial or pancreatic cancer (European Patent Specification No. 0400586). It is also known that EGF receptors which possess tyrosine kinase activity are over-expressed in many human cancers such as brain, lung squamous cell, bladder, gastric, breast, head and neck, esophageal, gynecological and thyroid tumors. Accordingly it has been recognized that an inhibitor of receptor tyrosine kinases should be of value as a selective inhibitor of the growth of mammalian cancer cells (Yaish et al. Science, 1988, 242, 933).

Compounds of this invention are thus of interest for the treatment of cancers, including both primary and metastatic cancers, including solid tumors as well as lymphomas and leukemias (including CML, AML and ALL), and including cancers which are resistant to other therapies, including other therapies involving the administration of inhibitors of Src, Abl, EGF-R, VEGF-R, PDGF-R, p38, kdr or other kinases, including inhibitors such as Gleevec, Tarceva and Iressa.

Such cancers include, among others, cancers of the breast, cervix, colon and rectum, lung, ovaries, pancreas, prostate, head and neck, gastrointestinal stroma, as well as diseases such as melanoma, multiple myeloma, non-Hodgkin's lymphoma, melanoma, gastric cancers and leukemias (e.g., myeloid, lymphocytic, myelocytic and lymphoblastic leukemias) including cases which are resistant to one or more other therapies, including among others kinase inhibitors such as mentioned above as well as other cancer therapeutics including those mentioned below.

Resistance to various anticancer agents can arise from one or more mutations in a mediator or effector of the cancer (e.g., mutation in a kinase such as Src or Abl) which correlate with alteration in the protein's drug binding properties, phosphate binding properties, protein binding properties, autoregulation or other characteristics. For example, in the case of BCR-Abl, the kinase associated with chronic myeloid leukemia, resistance to Gleevec has been mapped to a variety of BCR/Abl mutations which are linked to a variety of functional consequences, including among others, steric hindrance of drug occupancy at the kinase's active site, alteration in deformability of the phosphate binding P loop, effects on the conformation of the activation loop surrounding the active site, and others. See e.g. Shah et al, 2002, Cancer Cell 2, 117–125 and Azam et al, 2003, Cell 112, 831–843 and references cited therein for representative examples of such mutations in Bcr/Abl which correlate with drug resistance.

Again, we contemplate that compounds of this invention, both as monotherapies and in combination therapies, will be useful against tumors, leukemias and other cancers, including those which are resistant to one or more other anticancer agents, including among others tumors, leukemias and other cancers which are resistant in whole or part to other anticancer agents.

Pharmaceutical Methods

The method of the invention comprises administering to a subject in need thereof a therapeutically effective amount of a compound of the invention.

A "therapeutically effective amount" in the case of cancer therapeutics is that amount effective for detectable killing or inhibition of the growth or spread of cancer cells; the size or number of tumors; or other measure of the level, stage, progression or severity of the cancer. The exact amount required will vary from subject to subject, depending on the species, age, and general condition of the subject, the severity of the disease, the particular anticancer agent, its mode of administration, combination treatment with other therapies, and the like. The compound, or a composition containing the compound, may be administered using any amount and any route of administration effective for killing or inhibiting the growth of tumors or other forms of cancer.

The anticancer compounds of the invention are preferably formulated in dosage unit form for ease of administration and uniformity of dosage. The expression "dosage unit form" as used herein refers to a physically discrete unit of anticancer agent appropriate for the patient to be treated. As is normally the case, the total daily usage of the compounds and compositions of the present invention will be decided by the attending physician using routine reliance upon sound medical judgment. The specific therapeutically effective dose level for any particular patient or organism will depend upon a variety of factors including the disorder being treated; the severity of the disorder; the potency of the specific compound employed; the specific composition employed; the age, body weight, general health, sex and diet of the patient; the route and schedule of administration; the rate of metabolism and/or excretion of the compound; the duration of the treatment; drugs used in combination or coincident with administration of the compound of this invention; and like factors well known in the medical arts.

Furthermore, after formulation with an appropriate pharmaceutically acceptable carrier in a desired dosage, the compositions of this invention can be administered to humans and other animals orally, rectally, parenterally, intracisternally, intravaginally, intraperitoneally, topically (as by powders, ointments, or drops), bucally, as an oral or nasal spray, or the like.

The effective systemic dose of the compound will typically be in the range of 0.01 to 500 mg of compound per kg of patient body weight, preferably 0.1 to 125 mg/kg, and in some cases 1 to 25 mg/kg, administered in single or multiple doses. Generally, the compound may be administered to patients in need of such treatment in a daily dose range of about 50 to about 2000 mg per patient. Administration may be once or multiple times daily, weekly (or at some other multiple-day interval) or on an intermittent schedule. For example, the compound may be administered one or more times per day on a weekly basis (e.g. every Monday) indefinitely or for a period of weeks, e.g. 4–10 weeks. Alternatively, it may be administered daily for a period of days (e.g. 2–10 days) followed by a period of days (e.g. 1–30 days) without administration of the compound, with that cycle repeated indefinitely or for a given number of repititions, e.g. 4–10 cycles. As an example, a compound of the invention may be administered daily for 5 days, then discontinued for 9 days, then administered daily for another 5 day period, then discontinued for 9 days, and so on, repeating the cycle indefinitely, or for a total of 4–10 times.

The amount of compound which will be effective in the treatment or prevention of a particular disorder or condition will depend in part on well known factors affecting drug dosage. In addition, in vitro or in vivo assays may optionally be employed to help identify optimal dosage ranges. A rough guide to effective doses may be extrapolated from dose-response curves derived from in vitro or animal model test systems. The precise dosage level should be determined by the attending physician or other health care provider and will depend upon well known factors, including route of administration, and the age, body weight, sex and general health of the individual; the nature, severity and clinical stage of the disease; the use (or not) of concomitant therapies; and the nature and extent of genetic engineering of cells in the patient.

When administered for the treatment or inhibition of a particular disease state or disorder, the effective dosage of the compound of this invention may vary depending upon the particular compound utilized, the mode of administration, the condition, and severity thereof, of the condition being treated, as well as the various physical factors related to the individual being treated. In many cases, satisfactory results may be obtained when the compound is administered in a daily dosage of from about 0.01 mg/kg-500 mg/kg, preferably between 0.1 and 125 mg/kg, and more preferably between 1 and 25 mg/kg. The projected daily dosages are expected to vary with route of administration. Thus, parenteral dosing will often be at levels of roughly 10% to 20% of oral dosing levels.

When the compound of this invention is used as part of a combination regimen, dosages of each of the components of the combination are administered during a desired treatment period. The components of the combination may administered at the same time; either as a unitary dosage form containing both components, or as separate dosage units; the components of the combination can also be administered at different times during a treatment period, or one may be administered as a pretreatment for the other.

Regarding the Comgounds

Compounds of present invention can exist in free form for treatment, or where appropriate, as a pharmaceutically acceptable salt or other derivative. As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts of amines, carboxylic acids, phosphonates and other types of compounds, are well known in the art. For example, S. M. Berge, et al. describe pharmaceutically acceptable salts in detail in *J. Pharmaceutical Sciences,* 66: 1–19 (1977), incorporated herein by reference. The salts can be prepared in situ during the isolation and purification of the compounds of the invention, or separately by reacting the free base or free acid of a compound of the invention with a suitable base or acid, respectively. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hernisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Additionally, as used herein, the term "pharmaceutically acceptable ester" refers preferably to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, butyrates, acrylates and ethylsuccinates. Obviously, esters can be formed with a hydroxyl or carboxylic acid group of the compound of the invention.

Furthermore, the term "pharmaceutically acceptable prodrugs" as used herein refers to those prodrugs of the compounds of the present invention which are, within the scope of sound medical judgment, suitable for use in contact with the tissues of humans and lower animals with undue toxicity, irritation, allergic response, and the like, commensurate with a reasonable benefit/risk ratio, and effective for their intended use, as well as the zwitterionic forms, where possible, of the compounds of the invention. The term "prodrug" refers to compounds that are transformed in vivo to yield the parent compound of the above formula, for example by hydrolysis in blood. See, e.g., T. Higuchi and V. Stella, Pro-drugs as Novel Delivery Systems, Vol. 14 of the A.C.S. Symposium Series, and Edward B. Roche, ed., Bioreversible Carriers in Drug Design, American Pharmaceutical Association and Pergamon Press, 1987, both of which are incorporated herein by reference.

Compnositions

Accordingly, compositions are provided, which comprise any one of the compounds described herein (or a prodrug, pharmaceutically acceptable salt or other pharmaceutically acceptable derivative thereof, and one or more pharmaceutically acceptable carriers or excipients. These compositions optionally further comprise one or more additional therapeutic agents. Alternatively, a compound of this invention may be administered to a patient in need thereof in combination with the administration of one or more other therapeutic regimens (e.g. Gleevec or other kinase inhibitors, interferon, bone marrow transplant, farnesyl transferase inhibitors, bisphosphonates, thalidomide, cancer vaccines, hormonal therapy, antibodies, radiation, etc). For example, additional therapeutic agents for conjoint administration or inclusion in a pharmaceutical composition with a compound of this invention may be another one or more anticancer agents.

As described herein, the compositions of the present invention comprise a compound of the invention together with a pharmaceutically acceptable carrier, which, as used herein, includes any and all solvents, diluents, or other vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Fifteenth Edition, E. W. Martin (Mack Publishing Co., Easton, Pa., 1975) discloses various carriers used in formulating pharmaceutical compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutical composition, its use is contemplated to be within the scope of this invention. Some examples of materials which can serve as pharmaceutically acceptable carriers include, but are not limited to, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa bufter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition.

Formulations

This invention also encompasses a class of compositions comprising the active compounds of this invention (including those of Formula I, Formula II, Formulas I(a) through I(q) and the other compounds described herein) in association with one or more pharmaceutically-acceptable carriers and/or diluents and/or adjuvants (collectively referred to herein as "carrier" materials) and, if desired, other active ingredients. The active compounds of the present invention may be administered by any suitable route, preferably in the form of a pharmaceutical composition adapted to such a route, and in a dose effective for the treatment intended. The compounds and compositions of the present invention may, for example, be administered orally, mucosally, topically, rectally, pulmonarily such as by inhalation spray, or parentally including intravascularly, intravenously, intraperitoneally, subcutaneously, intramuscularly intrasternally and infusion techniques, in dosage unit formulations containing conventional pharmaceutically acceptable carriers, adjuvants, and vehicles.

The pharmaceutically active compounds of this invention can be processed in accordance with conventional methods of pharmacy to produce medicinal agents for administration to patients, including humans and other mammals.

For oral administration, the pharmaceutical composition may be in the form of, for example, a tablet, capsule, suspension or liquid. The pharmaceutical composition is preferably made in the form of a dosage unit containing a particular amount of the active ingredient.

Examples of such dosage units are tablets or capsules. For example, these may contain an amount of active ingredient from about 1 to 2000 mg, preferably from about 1 to 500 mg, more commonly from about 5 to 200 mg. A suitable daily dose for a human or other mammal may vary depending on the condition of the patient and other factors, but, once again, can be determined using routine methods.

The amount of compounds which are administered and the dosage regimen for treating a disease condition with the compounds and/or compositions of this invention depends on a variety of factors, including the age, weight, sex and medical condition of the subject, the type of disease, the severity of the disease, the route and frequency of administration, and the particular compound employed. Thus, the dosage regimen may vary widely, but can be determined routinely using standard methods. A typical daily dose is in the range of 0.01 to 500 mg of compound per kg body weight, preferably between 0.1 and 125 mg/kg body weight and in some cases between 1 and 25 mg/kg body weight. As mentioned previously, the daily dose can be given in one administration or may be divided between 2, 3, 4 or more administrations.

For therapeutic purposes, the active compounds of this invention are ordinarily combined with one or more adjuvants, excipients or carriers appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose.

In the case of skin conditions, it may be preferable to apply a topical preparation of compounds of this invention to the affected area two to four times a day.

Formulations suitable for topical administration include liquid or semi-liquid preparations suitable for penetration through the skin (e.g., liniments, lotions, ointments, creams, or pastes) and drops suitable for administration to the eye, ear, or nose. A suitable topical dose of active ingredient of a compound of the invention is 0.1 mg to 150 mg administered one to four, preferably one or two times daily. For topical administration, the active ingredient may comprise from 0.001% to 10% w/w, e.g., from 1% to 2% by weight of the formulation, although it may comprise as much as 10% w/w, but preferably not more than 5% w/w, and more preferably from 0.1% to 1% of the formulation.

When formulated in an ointment, the active ingredients may be employed with either paraffinic or a water-miscible ointment base. Alternatively, the active ingredients may be formulated in a cream with an oil-in-water cream base. If desired, the aqueous phase of the cream base may include, for example at Least 30% w/w of a polyhydric alcohol such as propylene glycol, butane-1,3-diol, mannitol, sorbitol, glycerol, polyethylene glycol and mixtures thereof. The topical formulation may desirably include a compound which enhances absorption or penetration of the active ingredient through the skin or other affected areas. Examples of such dermal penetration enhancers include dimethylsulfoxide and related analogs.

The compounds of this invention can also be administered by a transdermal device. Preferably transdermal administration will be accomplished using a patch either of the reservoir and porous membrane type or of a solid matrix variety. In either case, the active agent is delivered—continuously from the reservoir or microcapsules through a membrane into the active agent permeable adhesive, which is in contact with the skin or mucosa of the recipient. If the active agent is absorbed through the skin, a controlled and predetermined flow of the active agent is administered to the recipient. In the case of microcapsules, the encapsulating agent may also function as the membrane.

The oily phase of the emulsions of this invention may be constituted from known ingredients in a known manner. While the phase may comprise merely an emulsifier, it may comprise a mixture of at least one emulsifier with a fat or an oil or with both a fat and an oil. Preferably, a hydrophilic emulsifier is included together with a lipophilic emulsifier which acts as a stabilizer. It is also preferred to include both an oil and a fat. Together, the emulsifier(s) with or without stabilizer(s) make-up the socalled emulsifying wax, and the wax together with the oil and fat make up the so-called emulsifying ointment base which forms the oily dispersed phase of the cream formulations. Emulsifiers and emulsion stabilizers suitable for use in the formulation of the present invention include Tween 60, Span 80, cetostearyl alcohol, myristyl alcohol, glyceryl monostearate, sodium lauryl sulfate, glyceryl distearate alone or with a wax, or other materials well known in the art.

The choice of suitable oils or fats for the formulation is based on achieving the desired cosmetic properties, since the solubility of the active compound in most oils likely to be used in pharmaceutical emulsion formulations is very low. Thus, the cream should preferably be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters may be used. These may be used alone or in combination depending on the properties required.

Alternatively, high melting point lipids such as white soft paraffin and/or liquid paraffin or other mineral oils can be used.

Formulations suitable for topical administration to the eye also include eye drops wherein the active ingredients are dissolved or suspended in suitable carrier, especially an aqueous solvent for the active ingredients.

The active ingredients are preferably present in such formulations in a concentration of 0.5 to 20%, advantageously 0.5 to 10% and particularly about 1.5% w/w.

Formulations for parenteral administration may be in the form of aqueous or non-aqueous isotonic sterile injection solutions or suspensions. These solutions and suspensions may be prepared from sterile powders or granules using one or more of the carriers or diluents mentioned for use in the formulations for oral administration or by using other suitable dispersing or wetting agents and suspending agents. The compounds may be dissolved in water, polyethylene glycol, propylene glycol, ethanol, corn oil, cottonseed oil, peanut oil, sesame oil, benzyl alcohol, sodium chloride, tragacanth gum, and/or various buffers.

Other adjuvants and modes of administration are well and widely known in the pharmaceutical art. The active ingredient may also be administered by injection as a composition with suitable carriers including saline, dextrose, or water, or with cyclodextrin (i.e. Captisol), cosolvent solubilization (i.e. propylene glycol) or micellar solubilization (i.e. Tween 80).

The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed, including synthetic mono- or diglycerides. In addition, fatty acids such as oleic acid find use in the preparation of injectables.

For pulmonary administration, the pharmaceutical composition may be administered in the form of an aerosol or with an inhaler including dry powder aerosol.

Suppositories for rectal administration of the drug can be prepared by mixing the drug with a suitable nonirritating excipient such as cocoa butter and polyethylene glycols that are solid at ordinary temperatures but liquid at the rectal temperature and will therefore melt in the rectum and release the drug.

The pharmaceutical compositions may be subjected to conventional pharmaceutical operations such as sterilization and/or may contain conventional adjuvants, such as preservatives, stabilizers, wetting agents, emulsifiers, buffers etc. Tablets and pills can additionally be prepared with enteric coatings. Such compositions may also comprise adjuvants, such as wetting, sweetening, flavoring, and perfuming agents. Pharmaceutical compositions of this invention comprise a compound of the formulas described herein or a pharmaceutically acceptable salt thereof; an additional agent selected from a kinase inhibitory agent (small molecule, polypeptide, antibody, etc.), an immunosuppressant, an anti-cancer agent, an anti-viral agent, antiinflammatory agent, antifungal agent, antibiotic, or an anti-vascular hyperproliferation compound; and any pharmaceutically acceptable carrier, adjuvant or vehicle.

Alternate compositions of this invention comprise a compound of the formulae described herein or a pharmaceutically acceptable salt thereof; and a pharmaceutically acceptable carrier, adjuvant or vehicle. Such compositions may optionally comprise one or more additional therapeutic agents, including, for example, kinase inhibitory agents (small molecule, polypeptide, antibody, etc.), immunosuppressants, anti-cancer agents, anti-viral agents, antiinflammatory agents, antifungal agents, antibiotics, or anti-vascular hyperproliferation compounds.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, selfemulsifying drug delivery systems (SEDDS) such as d-atocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as u-, P-, and y-cyclodextrin, or chemically modified derivatives such as hydroxyalkylcyclodextrins, including 2and 3-hydroxypropyl-cyclodextrins, or other solubilized derivatives may also be advantageously used to enhance delivery of compounds of the formulae described herein.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents.

If desired, certain sweetening and/or flavoring and/or coloring agents may be added.

The pharmaceutical compositions of this invention may comprise formulations utilizing liposome or microencapsulation techniques, various examples of which are known in the art.

The pharmaceutical compositions of this invention may be administered by nasal aerosol or inhalation. Such compositions are prepared according to techniques well known in the art of pharmaceutical formulation and may be prepared as solutions in saline, employing benzyl alcohol or other suitable preservatives, absorption promoters to enhance bioavailability, fluorocarbons, and/or other solubilizing or dispersing agents, examples of which are also well known in the art.

Combinations

While the compounds of the invention can be administered as the sole active pharmaceutical agent, they can also be used in combination with one or more compounds of the invention or other agents. When administered as a combination, the therapeutic agents can be formulated as separate compositions that are administered at the same time-or sequentially at different times, or the therapeutic agents can be given as a single composition.

The phrase "co-therapy" (or "combination-therapy"), in defining use of a compound of this invention and another pharmaceutical agent, is intended to encompass administration of each agent in a sequential manner in a regimen that will provide beneficial effects of the drug combination, and is intended as well to embrace coadministration of these agents in a substantially simultaneous manner, such as in a single capsule having a fixed ratio of these active agents or in multiple, separate capsules for each agent.

Thus, the administration of compounds of the present invention may be in conjunction with additional therapies known to those skilled in the art in the prevention or treatment of cancer, such as radiation therapy or cytostatic or cytotoxic agents.

If formulated as a fixed dose, such combination products employ the compounds of this invention within the accepted dosage ranges. Compounds of this invention may also be administered sequentially with other anticancer or cytotoxic agents when a combination formulation is inappropriate. The invention is not limited in the sequence of administration; compounds of this invention may be administered prior to, simulateously with, or after administration of the other anticancer or cytotoxic agent.

Currently, standard treatment of primary tumors consists of surgical excision, when appropriate, followed by either radiation or chemotherapy, typically administered intravenously (IV). The typical chemotherapy regime consists of either DNA alkylating agents, DNA intercalating agents, CDK inhibitors, or microtubule poisons. The chemotherapy doses used are just below the maximal tolerated dose and therefore dose limiting toxicities typically include, nausea, vomiting, diarrhea, hair loss, neutropenia and the like.

There are large numbers of antineoplastic agents available in commercial use, in clinical evaluation and in pre-clinical development, which would be selected for treatment of cancer by combination drug chemotherapy. And there are several major categories of such antineoplastic agents, namely, antibiotic-type agents, alkylating agents, antimetabolite agents, hormonal agents, immunological agents, interferon-type agents and a category of miscellaneous agents.

A first family of antineoplastic agents which may be used in combination with compounds of the present invention includes antimetabolite-type/thymidilate synthase inhibitor antineoplastic agents. Suitable antimetabolite antineoplastic agents may be selected from but not limited to the group consisting of 5-FU-fhbrinogen, acanthifolic acid, aminothiadiazole, brequinar sodium, carmofur, CibaGeigy CGP-30694, cyclopentyl cytosine, cytarabine phosphate stearate, cytarabine conjugates, Lilly DATHF, Merrel Dow DDFC, dezaguanine, dideoxycytidine, dideoxyguanosine, didox, Yoshitomi DMDC, doxifluridine, Wellcome EHNA, Merck & Co. EX-015, fazarabine, floxuridine, fludarabine phosphate, 5fluorouracil, N-(21-furanidyl) fluorouracil, Daiichi Seiyaku FO-152, isopropyl pyrrolizine, Lilly LY-188011, Lilly LY-264618, methobenzaprim, methotrexate, Wellcome MZPES, norspermidine, NCI NSC-127716, NCI NSC-264880, NCI NSC-39661, NCI NSC-612567, Warner-Lambert PALA, pentostatin, piritrexim, plicamycin, Asahi Chemical PL-AC, Takeda TAC788, thioguanine, tiazofurin, Erbamont TIF, trimetrexate, tyrosine kinase inhibitors, Taiho UFT and uricytin. A second family of antineoplastic agents which may be used in combination with compounds of the present invention consists of alkylating-type antineoplastic agents. Suitable alkylating-type antineoplastic agents may be selected from but not limited to the group consisting of Shionogi 254-S, aldo-phosphamide analogues, altretamine, anaxirone, Boehringer Mannheim BBR-2207, bestrabucil, budotitane, Wakunaga CA-102, carboplatin, carmustine, Chinoin-139, Chinoin-153, chlorambucil, cisplatin, cyclophosphamide, American Cyanamid CL-286558, Sanofi CY-233, cyplatate, Degussa D 384, Sumimoto DACHP (Myr)2, diphenylspiromustine, diplatinum cytostatic, Erba distamycin derivatives, Chugai DWA-2114R, ITI E09, elmustine, Erbamont FCE-24517, estramustine phosphate sodium, fotemustine, Unimed G M, Chinoin GYKI-17230, hepsul-fam, ifosfamide, iproplatin, lomustine, mafosfamide, mitolactolf Nippon-41 Kayaku NK-121, NCI NSC-264395, NCI NSC-342215, oxaliplatin, Upjohn PCNU, prednimustine, Proter PTT-119, ranimustine, semustine, SmithKline SK&F-101772, Yakult Honsha SN-22, spiromus-tine, Tanabe Seiyaku TA-077, tauromustine, temozolomide, teroxirone, tetraplatin and trimelamol.

A third family of antineoplastic agents which may be used in combination with compounds of the present invention consists of antibiotic-type antineoplastic agents. Suitable antibiotic-type antineoplastic agents may be selected from but not limited to the group consisting of Taiho 4181-A, aclarubicin, actinomycin D, actinoplanone, Erbamont ADR-456, aeroplysinin derivative, Ajinomoto AN II, Ajinomoto AN3, Nippon Soda anisomycins, anthracycline, azino-mycin-A, bisucaberin, Bristol-Myers BL-6859, Bristol-Myers BMY-25067, Bristol-Myers BNY-25551, Bristol-Myers BNY-26605 IBristolMyers BNY-27557, Bristol-Myers BMY-28438, bleomycin sulfate, bryostatin-1, Taiho C-1027, calichemycin, chromoximycin, dactinomycin, daunorubicin, Kyowa Hakko DC-102, Kyowa Hakko DC-79, Kyowa Hakko DC-88A, Kyowa Hakko, DC89-AI, Kyowa Hakko DC92-B, ditrisarubicin B, Shionogi DOB41, doxorubicin, doxorubicin-fibrinogen, elsamicin-A, epirubicin, erbstatin, esorubicin, esperamicin-Al, esperamicin-Alb, Erbamont FCE21954, Fujisawa FK-973, fostriecin, Fujisawa FR-900482, glidobactin, gregatin-A, grincamycin, herbimycin, idarubicin, illudins, kazusamycin, kesarirhodins, Kyowa Hakko KM-5539, Kirin Brewery KRN-8602, Kyowa Hakko KT-5432, Kyowa Hakko KT-5594, Kyowa Hakko KT-6149, American Cyanamid LL-D49194, Meiji Seika ME 2303, menogaril, mitomycin, mitoxantrone, SmithKline M-TAG, neoenactin, Nippon Kayaku NK-313, Nippon Kayaku NKT-01, SRI International NSC-357704, oxalysine, oxaunomycin, peplomycin, pilatin, pirarubicin, porothramycin, pyrindanycin A, Tobishi RA-I, rapamycin (or other mTOR inhibitor including CCI779, RAD001 ("Everolimus") or one of the mTOR inhibitors disclosed in PCT/US03/03030), rhizoxin, rodorubicin, sibanomicin, siwenmycin, Sumitomo SM5887, Snow Brand SN-706, Snow Brand SN-07, sorangicin-A, -42 sparsomycin, SS Pharmaceutical SS-21020, SS Pharmaceutical SS-7313B, SS Pharmaceutical SS-9816B, steffimycin B, Taiho 4181-2, talisomycin, Takeda TAN-868A, terpentecin, thrazine, tricrozarin A, Upjohn U-73975, Kyowa Hakko UCN-10028A, Fujisawa WF-3405, Yoshitomi Y-25024 and zorubicin.

A fourth family of antineoplastic agents which may be used in combination with compounds of the present invention consists of a miscellaneous family of antineoplastic agents, including tubulin interacting agents, topoisomerase II inhibitors, topoisomerase I inhibitors and hormonal agents, selected from but not limited to the group consisting of (xcarotene, (X-difluoromethyl-arginine, acitretin, Biotec AD-5, Kyorin AHC-52, alstonine, amonafide, amphethinile, amsacrine, Angiostat, ankinomycin, anti-neoplaston A10, antineoplaston A2, antineoplaston A3, antineoplaston A5. antineoplaston AS2-1F Henkel APD, aphidicolin glycinate, asparaginase, Avarol, baccharin, batracylin, benfluron, benzotript, Ipsen-Beaufour BIM-23015, bisantrene, BristoMyers BNY-40481, Vestar boron-10, bromofosfamide, Wellcome BW-502, Wellcome BW-773, caracemide, carmethizole hydrochloride, Ajinomoto CDAF, chlorsulfaquinoxalone, Chemes CHX-2053, Chemex CHX-100, Warner-Lambert CI-921, WarnerLambert CI-937, Warner-Lambert CI-941, Warner-Lambert CI958, clanfenur, claviridenone, ICN compound 1259, ICN compound 4711, Contracan, Yakult Honsha CPT-11, crisnatol, curaderm, cytochalasin B.

cytarabine, cytocytin, Merz D-609, DABIS maleate, dacarbazine, datelliptinium, didemnin-B, dihaematoporphyrin ether, dihydrolenperone, dinaline, distamycin, Toyo Pharmar DM-341, Toyo Pharmar DM-75, Daiichi Seiyaku DN-9693, docetaxel elliprabin, elliptinium acetate, Tsumura EPMTC, the epothilones, ergotamine, etoposide, etretinate, fenretinide, Fujisawa FR-57704t gallium nitrate, genkwadaphnin, Chugai GLA43, Glaxo GR63178, grifolan NMF5N, hexadecylphosphocholine, Green Cross HO-221,-43 homoharringtonine, hydroxyurea, BTG ICRF-187, ilmofosine, isoglutamine, isotretinoin, Otsuka JI-36, Ramot K-477, Otsuak K-76COONa, Kureha Chemical K-AM, MECT Corp KI-8110, American Cyanamid L-623, leukoregulin, lonidamine, Lundbeck LU 1121 Lilly LY-186641, NCI (US) MAP, marycin, Merrel Dow MDL-27048, Medco MEDR-340, merbarone, merocyanine derivatives, methylanilinoacridine, Molecular Genetics MGI136, minactivin, mitonafide, mitoquidone mopidamol, motretinide, Zenyaku Kogyo MST-16, N-(retinoyl)amino acids, Nisshin Flour Milling N-021, N-acylated-dehydroalanines, nafazatrom, Taisho NCU-190, nocodazole derivative, Normosang, NCI NSC-145813, NCI NSC-361456, NCI NSC-604782, NCI NSC-95580, ocreotide, Ono ONO-112, oquizanocine, Akzo Org-10172, paclitaxel, pancratistatin, pazelliptine, Warner-Lambert PD-111707, Warner-Lambert PD-115934, Warner-Lambert PD-131141, Pierre Fabre PE-1001, ICRT peptide D, piroxantrone, polyhaematoporphyrin, polypreic acid, Efamol porphyrin, probimane, procarbazine, proglumide, Invitron protease nexin I, Tobishi RA-700, razoxane, Sapporo Breweries RBS, restrictin-P, retelliptine, retinoic acid, Rhone-Poulenc RP49532, Rhone-Poulenc RP-56976, SmithKline SK&F-104864, Sumitomo SM-108, Kuraray SMANCS, SeaPharm SP10094, spatol, spirocyclopropane derivatives, spirogermanium, Unimed, SS Pharmaceutical SS-554, strypoldinone, Stypoldione, Suntory SUN 0237, Suntory SUN 2071, superoxide dismutase, Toyama T-506, Toyama T-680, taxol, Teijin TEI-0303, teniposide, thaliblastine, Eastman Kodak TJB-29, tocotrienol, topotecan, Topostin, Teijin TT82, Kyowa Hakko UCN-01, Kyowa Hakko UCN-1028, ukrain, Eastman Kodak USB-006, vinblastine sulfate, vincristine, vindesine, vinestramide, vinorelbine, vintriptol, vinzolidine, withanolides and Yamanouchi YM Alternatively, the present compounds may also be used in co-therapies with other anti-neoplastic agents, such as −44 acemannan, aclarubicin, aldesleukin, alemtuzumab, alitretinoin, altretamine, amifostine, aminolevulinic acid, amrubicin, amsacrine, anagrelide, anastrozole, ANCER, ancestim, ARGLABIN, arsenic trioxide, BAM 002 (Novelos), bexarotene, bicalutamide, broxuridine, capecitabine, celmoleukin, cetrorelix, cladribine, clotrimazole, cytarabine ocfosfate, DA 3030 (Dong-A), daclizumab, denileukin diftitox, deslorelin, dexrazoxane, dilazep, docetaxel, docosanol, doxercalciferol, doxifluridine, doxorubicin, bromocriptine, carmustine, cytarabine, fluorouracil, HIT diclofenac, interferon alfa, daunorubicin, doxorubicin, tretinoin, edelfosine, edrecolomab eflornithine, emitefur, epirubicin, epoetin beta, etoposide phosphate, exemestane, exisulind, fadrozole, filgrastim, finasteride, fludarabine phosphate, formestane, fotemustine, gallium nitrate, gemcitabine, gemtuzumab zogamicin, gimeracil/oteracil/tegafur combination, glycopine, goserelin, heptaplatin, human chorionic gonadotropin, human fetal alpha fetoprotein, ibandronic acid, idarubicin, (imiquimod, interferon alfa, interferon alfa, natural, interferon alfa-2, interferon alfa-2a, interferon alfa-2b, interferon alfa-NI, interferon alfa-n3, interferon alfacon1, interferon alpha, natural, interferon beta, interferon beta-Ia, interferon beta-Ib, interferon gamma, natural interferon gamma-Ia, interferon gamma-Ib, interleukin-I beta, iobenguane, irinotecan, irsogladine, lanreotide, LC 9018 (Yakult), leflunomide, lenograstim, lentinan sulfate, letrozole, leukocyte alpha interferon, leuprorelin, levamisole+fluorouracil, liarozole, lobaplatin, lonidamine, lovastatin, masoprocol, melarsoprol, metoclopramide, mifepristone, miltefosine, mirimostim, mismatched double stranded RNA, mitoguazone, mitolactol, mitoxantrone, molgramostim, nafarelin, naloxone+pentazocine, nartograstim, nedaplatin, nilutamide, −45 noscapine, novel erythropoiesis stimulating protein, NSC 631570 octreotide, oprelvekin, osaterone, oxaliplatin, paclitaxel, pamidronic acid, pegaspargase, peginterferon alfa-2b, pentosan polysulfate sodium, pentostatin, picibanil, pirarubicin, rabbit antithymocyte polyclonal antibody, polyethylene glycol interferon alfa-2a, porfimer sodium, raloxifene, raltitrexed, rasburicase, rhenium Re 186 etidronate, RII retinamide, rituximab, romurtide, samarium (153 Sm) lexidronam, sargramostim, sizofiran, sobuzoxane, sonermin, strontium-89 chloride, suramin, tasonermin, tazarotene, tegafur, temoporfin, temozolomide, teniposide, tetrachlorodecaoxide, thalidomide, thymalfasin, thyrotropin alfa, topotecan, toremifene, tositumomab-iodine 131, trastuzumab, treosulfan, tretinoin, trilostane, trimetrexate, triptorelin, tumor necrosis factor alpha, natural, ubenimex, bladder cancer vaccine, Maruyama. vaccine, melanoma lysate vaccine, valrubicin, verteporfin, vinorelbine, VIRULIZIN, zinostatin stimalamer, or zoledronic acid; abarelix; AE 941 (Aeterna), ambamustine, antisense oligonucleotide, bcl-2 (Genta), APC 8015 (Dendreon), cetuximab, decitabine, dexaminoglutethimide, diaziquone, EL 532 (Elan), EM 800 (Endorecherche), eniluracil, etanidazole, fenretinidel filgrastim SDO1 (Amgen), fulvestrant, galocitabine, gastrin 17 immunogen, HLA-B7 gene therapy (Vical), granulocyte macrophage colony stimulating factor, histamine dihydrochloride, ibritumomab tiuxetan, ilomastat, IM 862 (Cytran), interleukin iproxifene, LDI 200 (Milkhaus), leridistim, lintuzumab, CA 125 MAb (Biomira), cancer MAb (Japan Pharmaceutical Development), HER-2 and Fc MAb (Medarex), idiotypic 105AD7 MAb (CRC Technology), idiotypic CEA MAb (Trilex), LYM iodine 131 MAb (Techniclone), polymorphic epithelial mucin-yttrium 90 MAb (Antisoma), marimastat, menogaril, mitumomab, motexafin, gadolinium, MX 6 (Galderma), nelarabine, nolatrexed, P 30–46 protein, pegvisomant, pemetrexed, porfiromycin, prinomastat, RL 0903 (Shire), rubitecan, satraplatin, sodium phenylacetate, sparfosic acid, SRL 172 (SR Pharma), SU 5416 (SUGEN)y SU 6668 (SUGEN), TA 077 (Tanabe), tetrathiomolybdate, thaliblastine, thrombopoietin, tin ethyl etiopurpurin, tirapazamine, cancer vaccine (Biomira), melanoma vaccine (New York University), melanoma vaccine (Sloan Kettering Institute), melanoma oncolysate vaccine (New York Medical College), viral melanoma cell lysates vaccine (Royal Newcastle Hospital), or valspodar.

Treatment Kits

In other embodiments, the present invention relates to a kit for conveniently and effectively carrying out the methods in accordance with the present invention. In general, the pharmaceutical pack or kit comprises one or more containers filled with one or more of the ingredients of the pharmaceutical compositions of the invention. Such kits are especially suited for the delivery of solid oral forms such as tablets or capsules. Such a kit preferably includes a number of unit dosages, and may also include a card having the dosages oriented in the order of their intended use. If desired, a memory aid can be provided, for example in the form of numbers, letters, or other markings or with a calendar insert, designating the days in the treatment schedule in which the dosages can be administered. Alternatively, placebo dosages, or calcium dietary supplements can be included to provide a kit in which a dosage is taken every day. Optionally associated with such container(s) can be a notice in the form prescribed by a governmental agency regulating the manufacture, use or sale of pharmaceutical products, which notice reflects approval by the agency of manufacture, use or sale for human administration.

The following representative examples contain important additional information, exemplification and guidance which can be adapted to the practice of this invention in its various embodiments and the equivalents thereof. These examples are intended to help illustrate the invention, and are not intended to, nor should they be construed to, limit its scope. Indeed, various modifications of the invention, and many further embodiments thereof, in addition to those shown and described herein, will become apparent to those skilled in the art upon review of this document, including the examples which follow and the references to the scientific and patent literature cited herein. The contents of those cited references are incorporated herein by reference to help illustrate the state of the art. In addition, for purposes of this invention, the chemical elements are identified in accordance with the Periodic Table of the Elements, CAS version, Handbook of Chemistry and Physics, 75$^{th}$ Ed., inside cover. Additionally, general principles of organic chemistry, as well as specific functional moieties and reactivity, are described in "Organic Chemistry", Thomas Sorrell, University Science Books, Sausalito: 1999, and "Organic Chemistry", Morrison & Boyd (3d Ed), the entire contents of both of which are incorporated herein by reference.

EXAMPLES

Example 1

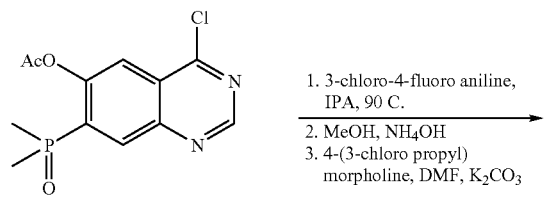

4-chloro-7-dimethyl-
phosphinoyl-
quinazolinol, acetate ester 1. 3-chloro-4-fluoro aniline, IPA, 90 C.
2. MeOH, NH$_4$OH
3. 4-(3-chloro propyl) morpholine, DMF, K$_2$CO$_3$

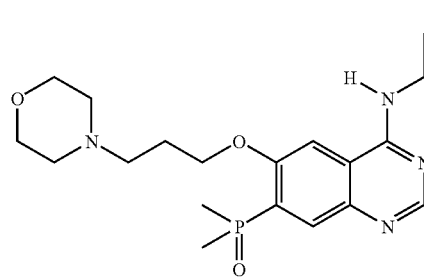

[3-chloro, 4fluro-phenyl]-[7-dimethylphosphinyl-6-(3morpholin-4-yl-propoxy)-quinazolin-4yl]-amine A mixture of 4-chloro-7-dimethylphosphinyl-6-quinazolinol, acetate ester (See e.g. PCT Int. Appl.(2001) WO 0104102 for the 7-methoxy analog and subsequent examples below for conversion of quinazinols to triflates followed by displacement with "J", our phosphorus-containing moiety) (3.2 mmol) and 3-chloro-4-flluoro aniline (3.3 mmol) in 2-propanol (20 mL) is heated at 90° C. for 10 hr. After this time the reaction mixture is cooled and the resulting product recovered to afford the 4-anilino-6-acetoxy quinazoline product. This material is then treated with MeOH (17 mL) followed by concentrated ammonium hydroxide and the resulting solution stirred for 17 h. After this time the reaction mixture is evaporated and the residue chromatographed on silica gel (10% MeOH/DCM) to afford deacetylated product.

The deacetylated intermediate is then dissolved in DMF (5 mL) and treated with K$_2$CO$_3$ (0.30 g, 2.18 mmol) followed by 4-(3-chloro propyl)morpholine (170 mg, 1.05 mmol). The resulting suspension is then heated at 100° C. for 24 h. After this time the reaction mixture is cooled, filtered, and evaporated to afford a residue that is triturated with 50% EtOAc/hexane to remove nonquinazoline-derived byproducts. The crude material is then purified by gradient RP (C-18) HPLC chromatography.

The following illustrative compounds may be prepared by analogous methods using the appropriately substituted aniline, aminobenzofuran, etc.:

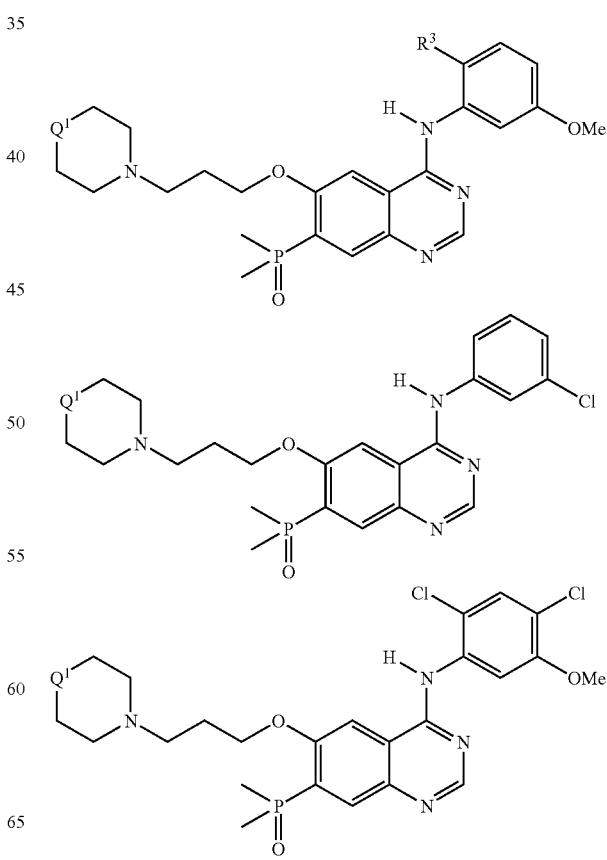

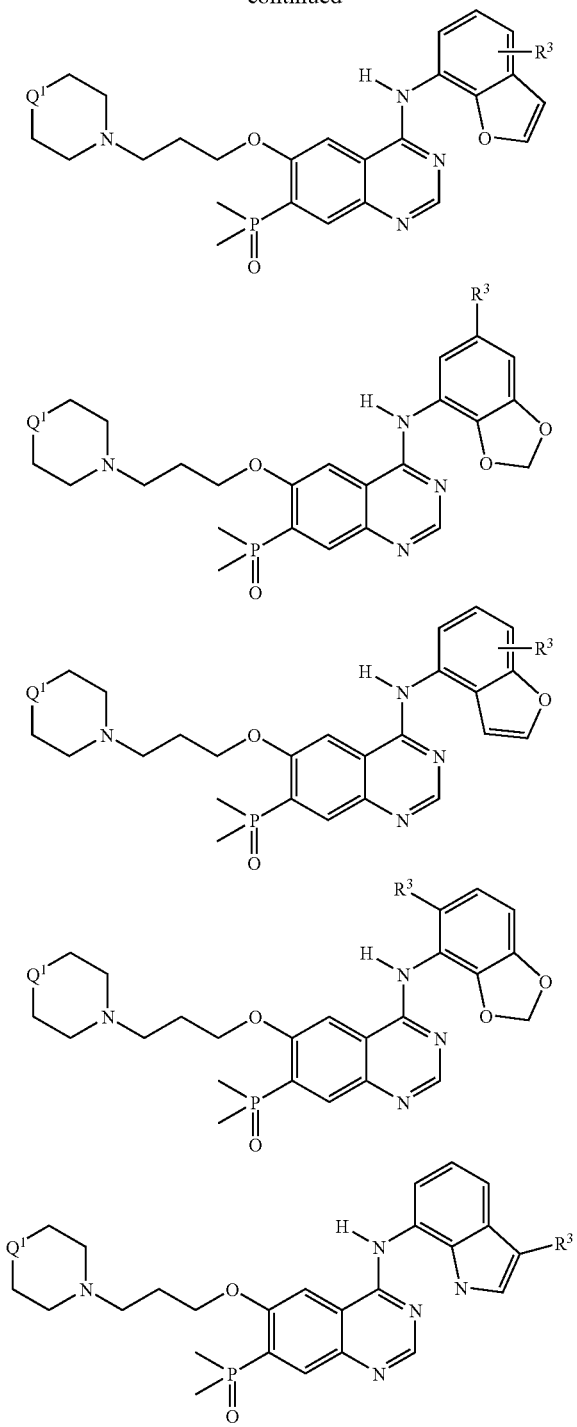

where R³ is H, Br, Cl, F or —OMe and Q¹ is O or N—Me.

Example 2

Preparation of 4-[(3-chloro-4-fluorophenyl)amino]-7-methoxy-6-quinzolinyl trifluoro-methanesulfonic acid ester A solution of 4-[(3-chloro-4-fluorophenyl)amino]-7-methoxy-6-quinazolinol (4.0 g, 12.5 mmoL) in anhydrous pyridine (80 mL) at −6° C. was treated dropwise with trifluoromethanesulphonic anhydride (2.3 mL, 13.7 mmol) while maintaining the internal reaction temperature between −5 to 0° C. The reaction was then allowed to warm to room temperature and stir overnight. After this time the reaction mixture was poured onto 700 mL of water, the resulting precipitate filtered, followed by crystallization with acetone (20 mL) by cooling to −20° C. The crystallized material was filtered and dried under vacuum at 50–60° C. to provide product (3.5 g, 62%) as a colorless solid: mp 191–192° C.; TLC (7.5% MeOH/CHCl₃) $R_f$=0.54; $^{19}$F NMR (DMSO-$d_6$, 75 MHz) −69.4 and −118.2; $^1$H NMR (DMSO-$d_6$, 300 MHz); 9.93 (s, 1 H), 8.68 (s, 1 H), 8.64 (s, 1 H), 8.11 (dd, J=6.8 and 2.6 Hz, 1 H), 7.80–7.74 (m, 1 H), 7.51 (s, 1 H), 7.46 (t, J=9.1 Hz, 1 H), 4.07 (s, 3 H); LRMS (ES−): (M−H)⁻ 450. Anal. Calcd for: C, 42.54; H, 2.23; N, 9.30; Cl, 7.85; F, 16.82; S. 7.10. Found: C, 42.37; H, 2.08; N, 9.12; Cl, 7.74; F, 16.70; S, 6.90.

Example 3

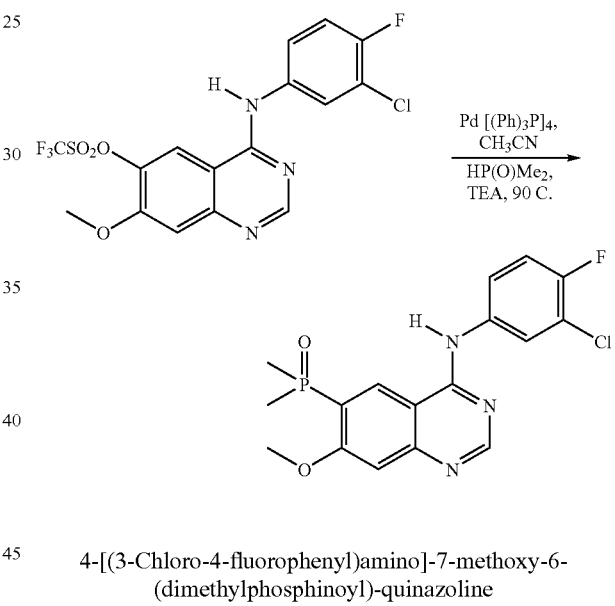

4-[(3-Chloro-4-fluorophenyl)amino]-7-methoxy-6-(dimethylphosphinoyl)-quinazoline A solution of 4-[(3-chloro-4-fluorophenyl)amino]-7-methoxy-6-quinazolinyl trifluoro-methanesulfonic acid ester (226 mg, 0.50 mmol), dimethylphosphine oxide (41 mg, 0.56 mmol), and tetrakis (triphenylphosphine)palladium (0) (58 mg, 0.05 mmol) in Argon-purged CH₃CN (1.5 mL) in a sealed vial was treated with triethylamine (106 uL, 0.75 mmol) and heated at 90° C. for 3 h. After this time the reaction mixture was cooled and the precipitated solids filtered with the aid of EtOAc. Solids were chromatographed on silica gel (4% MeOH/DCM) to afford product (155 mg, 82%) as a colorless solid: mp 257–259° C.; TLC (7.5% MeOH/CHCl₃) $R_f$=0.37; $^{19}$F NMR (CDCl₃, 75 MHz) −121.0; $^{31}$P NMR (CDCl₃, 75 MHz) 34.5; $^1$H NMR (CDCl₃, 300 MHz); 8.72 (d, J=14.2 Hz, 1 H), 8.62 (s, 1 H), 7.97 (dd, J=6.6 and 2.5 Hz, 1 H), 7.66–7.58 (m, 1 H), 7.53 (s, 1 H), 7.26–7.18 (m, 2 H), 4.07 (s, 3 H), 1.88 (d, J=13.9 Hz, 6 H); LRMS (ES+): (M+H)⁺ 380; (ES−): (M−H)⁻ 378.

Using methods analogous to those used in Examples 2 and 3, the following compounds may be similarly prepared:

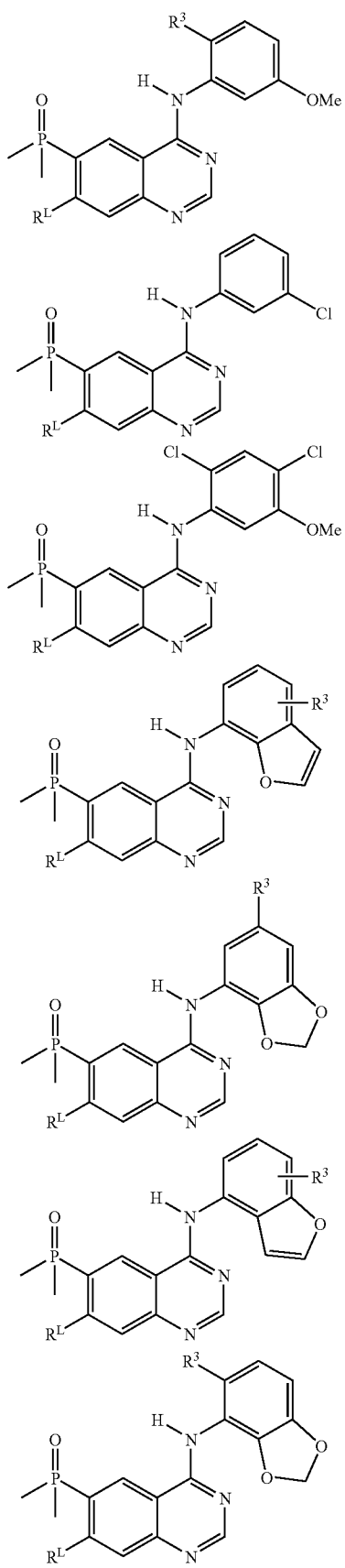

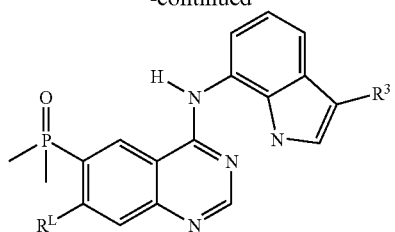

where R³ is H Br, Cl, F or —OMe and $R^L$ is 3-methoxypropoxy-, 3-morpholinopropoxy-, 3-(4-methylpiperazin-1-yl)propoxy-, 2-acetoxy-3-morpholinopropoxy-, 2-acetoxy-3-(N-isopropyl-N-methylamino)propoxy, 2-acetoxy-3-(4-cyanomethylpiperazin-1-yl)propoxy, 2-acetoxy-3-pyrrolidin-1-ylpropoxy or 2-acetoxy-3-piperidinopropoxy-.

Example 4

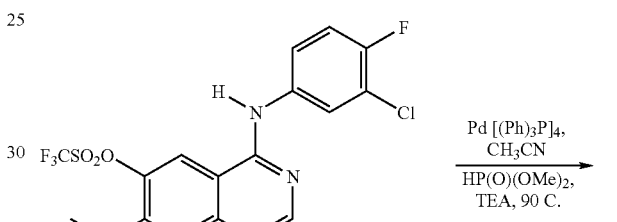

4-[(3-Chloro-4-fluorophenyl)amino]-7-methoxy-6-(dimethylphosphonate)-quinazoline A solution of 4-[(3-chloro-4-fluorophenyl)amino]-7-methoxy-6-(dimethylphosphonate)-quinazolinyl trifluoromethanesulfonic acid ester (452 mg, 1.00 mmol), dimethyl phosphite (97 uL, 1.05 mmol), and tetrakis(triphenylphosphine)palladium (0) (116 mg, 0.10 mmol) in Argon-purged $CH_3CN$ (1.5 mL) in a sealed vial was treated with triethylamine (211 uL, 1.50 mmol) and heated at 90° C. for 1.5 h. After this time the reaction mixture was cooled and the precipitated solids filtered with the aid of EtOAc. Solids were chromatographed on silica gel (2.5% MeOH/DCM) to afford product (91 mg, 22%) as a colorless solid: mp 283–285° C.; TLC (7.5% MeOH/CHCl₃) $R_f$=0.41; ¹⁹F NMR (CDCl₃, 75 MHz) −121.8; ³¹P NMR (CDCl₃, 75 MHz) 19.1; ¹H NMR (CDCl₃, 300 MHz); 9.50 (s, 1 H), 8.82 (d, J=16.8 Hz, 1 H), 8.66 (s, 1 H), 8.05 (dd, J=6.6 and 2.6 Hz, 1 H), 7.82–7.77 (m, 1 H), 7.18 (t, J=8.8), 6.98 (d, J=6.5, 1 H), 3.80–3.75 (m, 9 H); LRMS (ES+): (M+H)⁺ 412; (ES−): (M−H)⁻ 410.

Example 5

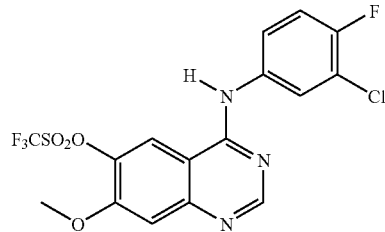

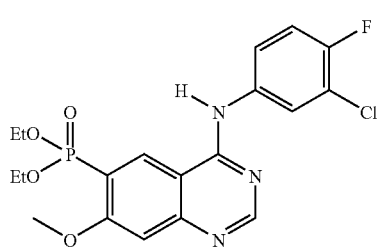

4-[(3-Chloro-4-fluorophenyl)amino]-7-methoxy-6-
(diethylphosphonate)-quinazoline A solution of 4-[(3-chloro-4fluorophenyl)amino]-7-methoxy-6-quinazolinyl trifluoro-methanesulfonic acid ester (452 mg, 1.00 mmol), diethyl phosphite (135 uL, 1.05 mmol), and tetrakis(triphenylphosphine)palladium (0) (116 mg, 0.10 mmol) in Argon-purged $CH_3CN$ (1.5 mL) in a sealed vial was treated with triethylamine (211 uL, 1.50 mmol) and heated at 90° C. for 1.5 h. After this time the reaction mixture was cooled and the precipitated solids filtered with the aid of EtOAc. Solids were chromatographed on silica gel (2.5% MeOH/DCM) to afford product (364 mg, 83%) as a colorless solid: mp 215–217° C.; TLC (7.5% MeOH/CHCl$_3$) R$_f$=0.46; $^{19}$F NMR (CDCl$_3$, 75 MHz) –121.8; $^{31}$P NMR (CDCl$_3$, 75 MHz) 15.9; $^1$H NMR (CDCl$_3$, 300 MHz); 9.60 (s, 1 H), 8.88 (d, J=16.8 Hz, 1 H), 8.67 (s, 1 H), 8.05 (dd, J=6.6 and 2.5 Hz, 1 H), 7.80–7.75 (m, 1 H), 7.17 (t, J=8.8, 1 H), 7.00 (d, J=6.4, 1 H), 4.18–4.00 (m, 4 H), 3.82 (s, 3 H), 1.26 (t, J=7.1 Hz, 3 H); LRMS (ES+): (2M+H)+879; (ES−): (M−H)⁻ 438.

Example 6

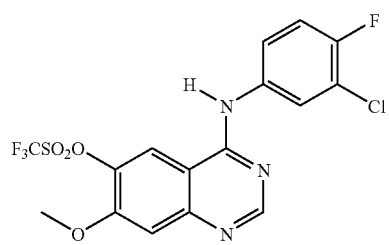

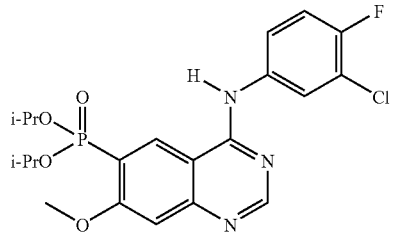

4-[(3-Chloro-4-fluorophenyl)amino]-7-methoxy-6-
(diisopropylphosphonate)-quinazoline A solution of 4-[(3-chloro-4-fluorophenyl)amino]-7-methoxy-6-quinazolinyl trifluoro-methanesulfonic acid ester (452 mg, 1.00 mmol), diisopropyl phosphite (175 uL, 1.05 mmol), and tetrakis(triphenylphosphine)palladium (0) (116 mg, 0.10 mmol) in Argon-purged $CH_3CN$ (1.5 mL) in a sealed vial was treated with triethylamine (211 uL, 1.50 mmol) and heated at 90° C. for 1.5 h. After this time the reaction mixture was cooled and the precipitated solids filtered with the aid of EtOAc. Solids were chromatographed on silica gel (2.5% MeOH/DCM) to afford product (121 mg, 26%) as a colorless solid: mp 192–193° C.; TLC (7.5% MeOH/CHCl$_3$) R$_f$=0.49; $^{19}$F NMR (CDCl$_3$, 75 MHz) –121.6; $^{31}$P NMR (CDCl$_3$, 75 MHz) 12.9; $^1$H NMR (CDCl$_3$, 300 MHz); 9.68 (s, 1 H), 9.08 (d, J=16.8 Hz,1 H), 8.70 (s, 1 H), 8.01 (dd, J=6.5 and 2.4 Hz, 1 H), 7.76–7.71 (m, 1 H), 7.19–7.13 (m, 2 H), 4.57–4.46 (m, 2 H), 3.93 (s, 3 H),1.17 (d, J=6.1 Hz, 6 H) 1.05 (d, J=6.1 Hz, 6 H); LRMS (ES+): (M+H)⁺ 380; (ES−): (M−H)⁻ 378.

Example 7

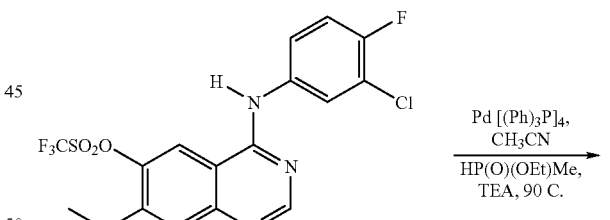

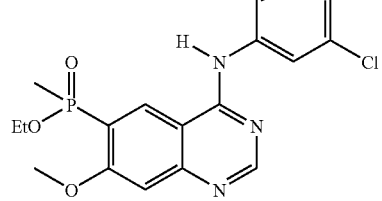

4-[(3-Chloro-4-fluorophenyl)amino]-7-methoxy-6-
(ethyl-methylphosphinate)-quinazoline A solution of 4-[(3-chloro-4-fluorophenyl)amino]-7-methoxy-6-quinazolinyl trifluoro-methanesulfonic acid ester (452 mg, 1.00 mmol), ethyl methylphosphinate (114 uL, 1.05 mmol), and tetrakis(triphenylphosphine)palladium (0) (116 mg, 0.10 mmol) in Argon-purged CH$_3$CN (1.5 mL) in a sealed vial was treated with triethylamine (211 uL, 1.50 mmol) and heated at 90° C. for 3 h. After this time the reaction mixture was cooled, evaporated and the residue chromatographed on silica gel (2.5% MeOH/DCM) to afford product (380 mg, 93%) as a colorless solid: mp 199–200° C.; TLC (7.5% MeOH/CHCl$_3$) R$_f$=0.46; $^{19}$F NMR (CDCl$_3$, 75 MHz) −121.2; $^{31}$P NMR (CDCl$_3$, 75 MHz) 40.5; $^1$H NMR (CDCl$_3$, 300 MHz); 10.36 (s, 1 H), 9.36 (d, J=14.5 Hz,1 H), 8.69 (s, 1 H), 7.95 (dd, J=6.6 and 2.5 Hz, 1 H), 7.78–7.73 (m, 1 H), 7.30–7.16 (m, 2 H), 4.00 (s, 3 H), 3.95–3.83 (m, 1 H), 3.71–3.62 (m, 1 H), 1.61 (d, J=15.5 Hz, 3 H) 1.10 (d, J=7.0 Hz, 3 H); LRMS (ES+): (M+H)+ 410; (ES−): (M−H)⁻ 408.

Using analgous methods the following compounds may also be prepared:

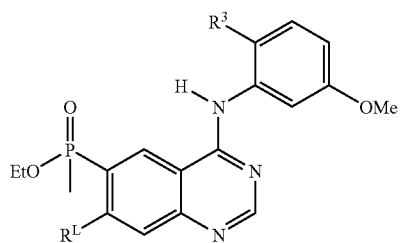

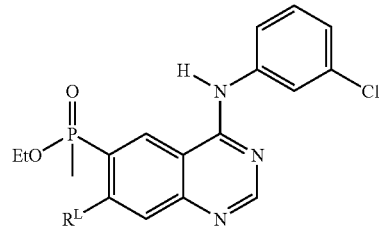

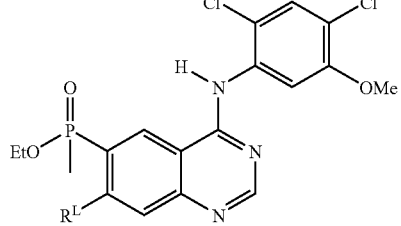

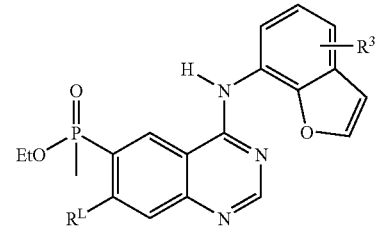

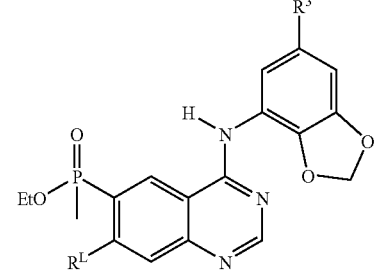

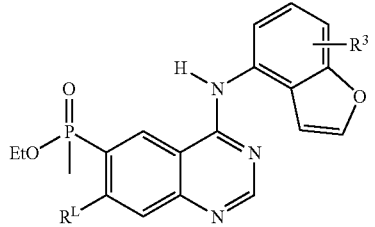

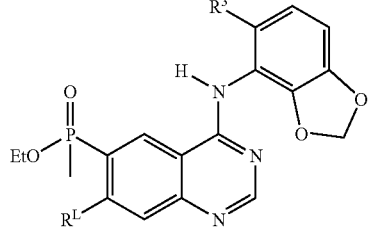

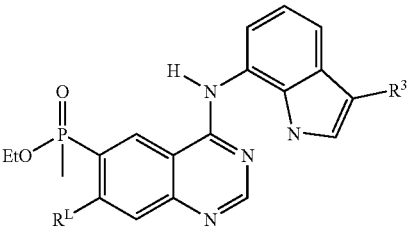

where R$^3$ is H, Br, Cl, F or —OMe and R$^L$ is 3-methoxypropoxy-, 3-morpholinopropoxy-, 3-(4methylpiperazin-1-yl)propoxy-, 2-acetoxy-3-morpholinopropoxy-, 2-acetoxy-3-(N-isopropyl-N-methylamino)propoxy, 2-acetoxy-3-(4-cyanomethylpiperazin-1-yl)propoxy, 2-acetoxy-3-pyrrolidin-1-ylpropoxy or 2-acetoxy-3-piperidinopropoxy-.

Example 8

Pharmaceutical Compositions

The following illustrate representative pharmaceutical dosage forms of the compounds of this invention (the active ingredient being referred to as "Compound"), for therapeutic or prophylactic use in humans.

| (a) Tablet I | mg/tablet |
|---|---|
| Compound | 100 |
| Lactose Ph. Eur | 182.75 |
| Croscarmellose sodium | 12.0 |
| Maize starch paste (5% w/v paste) | 2.25 |
| Magnesium stearate | 3.0 |

| (b) Tablet II | mg/tablet |
|---|---|
| Compound | 50 |
| Lactose Ph. Eur | 223.75 |
| Croscarmellose sodium | 6.0 |
| Maize starch | 15.0 |
| Polyvinylpyrrolidone (5% w/v paste) | 2.25 |
| Magnesium stearate | 3.0 |

| (c) Tablet III | mg/tablet |
|---|---|
| Compound | 1.0 |
| Lactose Ph. Eur | 93.25 |
| Croscarmellose sodium | 4.0 |
| Maize starch paste (5% w/v paste) | 0.75 |
| Magnesium stearate | 1.0–76 |

| (d) Capsule | mg/capsule |
|---|---|
| Compound | 10 |
| Lactose Ph. Eur | 488.5 |
| Magnesium | 1.5 |

| (e) Injection I | (50 mg/ml) |
|---|---|
| Compound | 5.0% w/v |
| 1 M Sodium hydroxide solution | 15.0% v/v |
| 0.1 M Hydrochloric acid (to adjust pH to 7.6) | |
| Polyethylene glycol 400 | 4.5% w/v |
| Water for injection to 100% | |

| (f) Injection II | (10 mg/ml) |
|---|---|
| Compound | 1.0% W/v |
| Sodium phosphate BP | 3.6% w/v |
| 0.1 M Sodium hydroxide solution | 15.0% v/v |
| Water for injection to 100% | |

| (g) Injection III | (1 mg/ml, buffered to pH6) |
|---|---|
| Compound | 0.1% w/v |
| Sodium phosphate BP | 2.26% w/v |
| Citric acid | 0.38% w/v |
| Polyethylene glycol 400 | 3.5% w/v |
| Water for injection to 100% | |

| (h) Aerosol | 1 mg/ml |
|---|---|
| Compound | 10.0 |
| Sorbitan trioleate | 13.5 |
| Trichlorofluoromethane | 910.0 |
| Dichlorodifluorometha-ne | 490.0 |

| (i) Aerosol II | mg/ml |
|---|---|
| Compound | 0.2 |
| Sorbitan trioleate | 0.27 |
| Trichlorofluoromethane | 70.0 |
| Dichlorodifluoromethane | 280.0 |
| Dichlorotetrafluoroethane | 1094.0 |

| (j) Aerosol III | mg/ml |
|---|---|
| Compound | 2.5 |
| Sorbitan trioleate | 3.38 |
| Trichlorofluoromethane | 67.5 |
| Dichlorodifluoromethane | 1086.0 |
| Dichlorotetrafluoroethane | 191.6 |

| (k) Aerosol IV | mg/ml |
|---|---|
| Compound | 2.5 |
| Soya lecithin | 2.7 |
| Trichlorofluoromethane | 67.5 |
| Dichlorodifluoromethane | 1086.0 |
| Dichlorotetrafluoroethane | 191.6 |

| (l) Ointment | ml |
|---|---|
| Compound | 40 mg |
| Ethanol | 300 μl |
| Water | 300 μl |
| 1-Dodecylazacycloheptan one | 50 μl |
| Propylene glycol | to 1 ml |

Note:
These formulations may be prepared using conventional procedures well known in the pharmaceutical art. The tablets (a)–(c) may be enteric coated by conventional means, if desired to provide a coating of cellulose acetate phthalate, for example. The aerosolformulations (h)–(k) may be used in conjunction with standard, metered dose aerosol dispensers, and the suspending agents sorbitan trioleate and soya lecithin may be replaced by an alternative suspending agent such as sorbitan monooleate, sorbitan sesquioleate, polysorbate 80, polyglycerol oleate or oleic acid.

Example 9

Biological Evaluation of Compounds

Compounds of this invention may be evaluated in a variety of assays to determine their biological activities. For example, the compounds of the invention can be tested for their ability to inhibit various protein kinases of interest. The compounds can also be evaluated for their cytotoxic and growth inhibitory effects on tumor cells of interest. See e.g., WO 03/000188, pages 115–136, the full contents of which are incorporated herein by reference.

Kinase Inhibition

More specifically, the compounds described herein are screened for kinase inhibition activity as follows. Kinases suitable for use in the following protocol include, but are not limited to: Abl, Lck, Lyn, Src, Fyn, Syk, Zap-70, Itk, Tec, Btk, EGFR, ErbB2, Kdr, Flt1, Flt-3, Tek, c-Met, InsR, and AKT.

Kinases are expressed as either kinase domains or full length constructs fused to glutathione S-transferase (GST) or polyHistidine tagged fusion proteins in either *E. coli* or Baculovirus-High Five expression systems. They are purified to near homogeneity by affinity chromatography as previously described (Lehr et al., 1996; Gish et al., 1995). In some instances, kinases are co-expressed or mixed with purified or partially purified regulatory polypeptides prior to measurement of activity.

Kinase activity and inhibition are measured by established protocols (see e.g., Braunwalder et al., 1996). Briefly, the transfer of $^{33}PO_4$ from ATP to the synthetic substrates poly (Glu, Tyr) 4:1 or poly(Arg, Ser) 3:1 attached to the bioactive surface of microtiter plates is taken as a measure of enzyme activity. After an incubation period, the amount of phosphate transferred is measured by first washing the plate with 0.5% phosphoric acid, adding liquid scintillant, and then counting in a liquid scintillation detector. The IC50 is determined by the concentration of compound that causes a 50% reduction in the amount of $^{33}P$ incorporated onto the substrate bound to the plate.

Other methods relying upon the transfer of phosphate to peptide or polypeptide substrate containing tyrosine, serine, threonine or histidine, alone, in combination with each other, or in combination with other amino acids, in solution or immobilized (i.e., solid phase) are also useful.

For example, transfer of phosphate to a peptide or polypeptide can also be detected using scintillation proximity, Fluorescence Polarization and homogeneous time-resolved fluorescence. Alternatively, kinase activity can be measured using antibody-based methods in which an antibody or polypeptide is used as a reagent to detect phosphorylated target polypeptide.

For additional background information on such assay methodologies, see e,.g., Braunwalder et al., 1996, Anal. Biochem. 234(I):23; Cleaveland et al., 1990, Anal Biochem. 190(2):249 Gish et al. (1995). Protein Eng. 8(6):609 Kolb et al. (1998). Drug Discov. Toda V. 3:333 Lehr et al. (1996). Gene 169(2):27527–87 Seethala et al. (1998). Anal Biochem. 255(2):257 Wu et al. (2000).

IC50 values in the single digit nanomolar—single digit micromolar range have been observed for compounds of this invention against EGF-R kinase.

Cell-based Assays

Certain compounds of this invention have also been demonstrated cytotoxic or growth inhibitory effects on tumor and other cancer cell lines and thus may be useful in the treatment of cancer and other cell proliferative diseases. Compounds are assayed for anti-tumor activity using in vivo and in vitro assays which are well known to those skilled in the art. Generally, initial screens of compounds to identify candidate anti-cancer drugs are performed in cellular assays. Compounds identified as having anti-proliferative activity in such cell-based assays can then be subsequently assayed in whole organisms for anti-tumor activity and toxicity. Generally speaking, cell-based screens can be performed more rapidly and cost-effectively relative to assays that use whole organisms. For purposes of this invention, the terms "anti-tumor" and "anti-cancer" activity are used interchangeably.

Cell-based methods for measuring antiproliferative activity are well known and can be used for comparative characterization of compounds of this invention. In general, cell proliferation and cell viability assays are designed to provide a detectable signal when cells are metabolically active. Compounds may be tested for antiproliferative activity by measuring any observed decrease in metabolic activity of the cells after exposure of the cells to compound. Commonly used methods include, for example, measurement of membrane integrity (as a measure of cell viability)(e.g. using trypan blue exclusion) or measurement of DNA synthesis (e.g. by measuring incorporation of BrdU or 3H-thymidine).

Some methods for assaying cell proliferation use a reagent that is converted into a detectable compound during cell proliferation. Particularly preferred compounds are tetrazolium salts and include without limitation MTT (3-(4, 5-dimethylthiazol-2-yl)-2,5-diphenyltetrazolium bromide; Sigma-Aldrich, St. Louis, Mo.), MTS (3-(4,5-dimethylthiazol-2-yl)-5-(3-carboxymethoxyphenyl)-2-(4-sulfophenyl)-2H-tetrazolium), XTT (2,3-bis(2-Methoxy4-nitro-5-sulfophenyl)-2H-tetrazolium-5-carboxanilide), INT, NBT, and NTV (Bernas et al. Biochim Biophys Acta 1451(1):73–81, 1999). Preferred assays utilizing tetrazolium salts detect cell proliferation by detecting the product of the enzymatic conversion of the tetrazolium salts into blue formazan derivatives, which are readily detected by spectroscopic methods (Mosman. J. Immunol. Methods. 65:55–63, 1983).

Generally, preferred methods for assaying cell proliferation involve incubating cells in a desired growth medium with and without the compounds to be tested. Growth conditions for various prokaryotic and eukaryotic cells are well-known to those of ordinary skill in the art (Ausubel et al. Current Protocols in Molecular Biology. Wiley and Sons. 1999; Bonifacino et al. Current Protocols in Cell Biology. Wiley and Sons. 1999 both incorporated herein by reference). To detect cell proliferation, the tetrazolium salts are added to the incubated cultured cells to allow enzymatic conversion to the detectable product by active cells. Cells are processed, and the optical density of the cells is determined to measure the amount of formazan derivatives. Furthermore, commercially available kits, including reagents and protocols, are available for examples, from Promega Corporation (Madison, Wis.), Sigma-Aldrich (St. Louis, Mo.), and Trevigen (Gaithersburg, Md.).

A wide variety of cell types may be used to screen compounds for antiproliferative activity, including the following cell lines, among others: COLO 205 (colon cancer), DLD-1 (colon cancer), HCT-15 (colon cancer), HT29 (colon cancer), HEP G2 (Hepatoma), K-562 (Leukemia), A549 (Lung), NCI-H249 (Lung), MCF7 (Mammary), MDA-MB-231 (Mammary), SAOS-2 (Osteosarcoma), OVCAR-3 (Ovarian), PANC-1 (Pancreas), DU-145 (Prostate), PC-3 (Prostate), ACHN (Renal), CAKI-1 (Renal), MG-63 (Sarcoma). The MDA468 tumor cell line is particularly useful for screening EGF-R inhibitors.

Preferably, the cell line is a mammalian, but is not limited to mammalian cells since lower order eukaryotic cells such as yeast may also be used to screen compounds. Preferred mammalian cell lines are derived from humans, rats, mice, rabbits, monkeys, hamsters, and guinea pigs since cells lines from these organisms are well-studied and characterized. However, others may be used as well.

Suitable mammalian cell lines are often derived from tumors. For example, the following tumor cell-types may be sources of cells for culturing cells: melanoma, myeloid leukemia, carcinomas of the lung, breast, ovaries, colon, kidney, prostate, pancreas and testes), cardiomyocytes, endothelial cells, epithelial cells, lymphocytes (T-cell and B cell), mast cells, eosinophils, vascular intimal cells, hepatocytes, leukocytes including mononuclear leukocytes, stem cells such as haemopoetic, neural, skin, lung, kidney, liver and myocyte stem cells (for use in screening for differentiation and de-differentiation factors), osteoclasts, chondrocytes and other connective tissue cells, keratinocytes, melanocytes, liver cells, kidney cells, and adipocytes. Non-limiting examples of mammalian cells lines that have been widely used by researchers include HeLa, NIH/3T3, HT1080, CHO, COS-1, 293T, WI-38 and CV1/EBNA-1.

Other cellular assays may be used which rely upon a reporter gene to detect metabolically active cells. Non-limiting examples of reporter gene expression systems include green fluorescent protein (GFP), and luciferase. As an example of the use of GFP to screen for potential antitumor drugs, Sandman et al. (Chem Biol. 6:541–51; incorporated herein by reference) used HeLa cells containing an inducible variant of GFP to detect compounds that inhibited expression of the GFP, and thus inhibited cell proliferation.

Compounds identified by such cellular assays as having anti-cell proliferation activity are then tested for anti-tumor activity in whole organisms. Preferably, the organisms are mammalian. Well-characterized mammalians systems for studying cancer include rodents such as rats and mice. Typically, a tumor of interest is transplanted into a mouse having a reduced ability to mount an immune response to the tumor to reduce the likelihood of rejection. Such mice include for example, nude mice (athymic) and SCID (severe combined immunodeficiency) mice. Other transgenic mice such as oncogene containing mice may be used in the present assays (see for example U.S. Pat. Nos. 4,736,866 and 5,175,383). For a review and discussion on the use of rodent models for antitumor drug testing see Kerbel (Cancer Metastasis Rev. 17:301–304, 1998–99).

In general, the tumors of interest are implanted in a test organism preferably subcutaneously. The organism containing the tumor is treated with doses of candidate anti-tumor compounds. The size of the tumor is periodically measured to determine the effects of the test compound on the tumor. Some tumor types are implanted at sites other than subcutaneous sites (e.g. intraperitoneal sites) and survival is measured as the endpoint. Parameters to be assayed with routine screening include different tumor models, various tumor and drug routes, and dose amounts and schedule. For a review of the use of mice in detecting antitumor compounds see Corbett et al. (Invest New Drugs. 15:207–218, 1997; incorporated herein by reference).

The compounds of Examples 3, 5 and 7 which were tested for inhibitory activity against the EGF-R kinase were found to have IC50 values in the range of about 0.06–1.6 µM and those which were tested in a conventional cell-based assay against the MDA-468 tumor cell line were found to have IC50 values under 50 µM, comparable in some cases to the value obtained for the potent kinase inhibitor, Iressa.

The invention claimed is:

1. A compound of the formula (I):

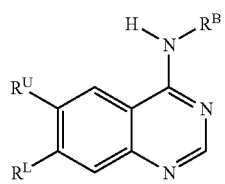

Formula I wherein:
$R^B$ is a substituted or unsubstituted aryl or heteroaryl moiety;
at least one of $R^U$ and $R^L$ is a phosphorus-containing moiety, J, which is covalently linked to the quinazoline ring through a carbon-phosphorous bond,
and the other of $R^U$ and $R^L$ is independently chosen from H; halogen; —CN; —NO$_2$; -J; —SO$_2$R; —SO$_2$NRR'; or -ZR$^J$, wherein each occurrence of Z is independently —O—, —S— or —NR— and each occurrence of R$^J$ is independently —R, —COR, —COOR or —CONRR';
each occurrence of R, R', without further alphanumeric designation, is independently hydrogen, or an aliphatic, heteroaliphatic, aryl or heteroaryl moiety;

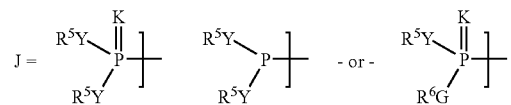

K is O or S;
each occurrence of Y is independently —O—, —S—, —NR—, or a chemical bond;
each occurrence of $R^5$ is independently an aliphatic, heteroaliphatic, aryl or heteroaryl moiety, or (except when attached directly to P) $R^5$ may be H;
each occurrence of $R^6$ is independently $R^5$, -PK(YR$^5$)(YR$^5$), —SO$_2$(YR$^5$) or —C(O)(YR$^5$)
wherein two of the $R^5$ and/or $R^6$ moieties may be chemically linked to one another to form a ring;
each occurrence of G is independently —O—, —S—, —NR— or $M_X$;
each occurrence of $M_X$ is independently a 1–6 carbon aliphatic moiety; and
in each of the foregoing groups each aliphatic or heteroaliphatic moiety contains 1–10 aliphatic carbon atoms and may be branched or unbranched, cyclic or acyclic, substituted or unsubstituted, and may contain one or more electronically unsaturated bonds; and each aryl and heteroaryl moiety may be substituted or unsubstituted.

2. The compound of claim 1 wherein J is a moiety of one of the following structures:

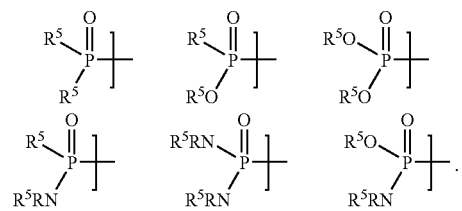

3. The compound of claim 1 wherein $R^U$ or $R^L$ is a moiety of the formula -ZR$^J$, wherein Z is O or NR and R$^J$ is R or —H(CO)R and each R is a substituted or unsubstituted aliphatic, heteroaliphatic, aryl, or heteroaryl moiety.

4. The compound of claim 3 wherein $R^U$ or $R^L$ is MeO—, EtO—, MeOCH$_2$CH$_2$O—, MeOCH$_2$CH$_2$CH$_2$O—, CH$_2$=CHCH$_2$O—, CHCCH$_2$O—, -ZR$^J$ or a heterocylic moiety, ZR$^J$, wherein Z is O and R$^J$ is a substituted aliphatic moiety chosen from 1–6 carbon aliphatic moieties beraring a substituent J.

5. The compound of the formula:

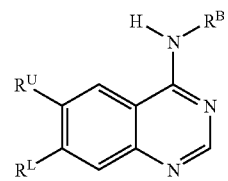

wherein
$R^B$ is a substituted or unsubstituted aryl or heteroaryl moiety;

at least one one of $R^U$ and $R^L$ is a phosphorus-containing moiety, J, which is covalently linked to the quinazoline ring through a carbon-phosphorous bond, and the other $R^U$ and $R^L$ a hydroxy, amion, carboxy, carbamoyl, ureidom, ($C_{1-4}$)alkoxycarbonyl, N—($C_{1-4}$)alkylcarbamoyl, N,N-di-[($C_{1-4}$)alkyl]carbamoyl, hydroxyamino, ($C_{1-4}$)alkoxyamino, ($C_{2-4}$)alkanoyloxyamino, trifluoromethoxy, ($C_{1-4}$)alkyl, 6-($C_{1-4}$)alkoxy, 7-($C_{1-4}$)alkoxy, ($C_{1-3}$)alkylenedioxy, ($C_{1-4}$)alkylamino, di-[($C_{1-4}$)alkyl]amino, pyrrolidin-1-yl, piperidino, morpholino, piperazin-1-yl, 4-($C_{1-4}$)alkylpiperazin-1-yl, ($C_{1-4}$)alkylthio, ($C_{1-4}$)alkylsulphinyl, ($C_{1-4}$)alkylsulphonyl, bromomethyl, dibromomethyl, hydroxy-($C_{1-4}$)alkyl, ($C_{2-4}$)alkanoyloxy-($C_{1-4}$)alkyl, ($C_{1-4}$)alkoxy-($C_{1-4}$)alkyl, carboxy-($C_{1-4}$)alkyl, ($C_{1-4}$)alkoxycarbonyl-($C_{1-4}$)alkyl, carbamoyl-($C_{1-4}$)alkyl, N—($C_{1-4}$)alkylcarbamoyl-($C_{1-4}$)alkyl, N, N-di-[($C_{1-4}$)alkyl]carbamoyl-($C_{1-4}$)alkyl, amino-($C_{1-4}$)alkyl, ($C_{1-4}$)alkylamino-($C_{1-4}$)alkyl, di-[($C_{1-4}$)alkyl]amino-($C_{1-4}$)alkyl, piperidino-($C_{1-4}$)alkyl, morpholino-($C_{1-4}$)alkyl, piperazin-1-yl-($C_{1-4}$) alkyl, 4-($C_{1-4}$)alkylpiperazin-1-yl-($C_{1-4}$)alkyl, hydroxy-($C_{2-4}$)alkoxy-($C_{1-4}$)alkyl, ($C_{1-4}$)alkoxy-($C_{2-4}$)alkoxy-($C_{1-4}$)alkyl hydroxy-($C_{2-4}$)alkylamino-($C_{1-4}$)alkyl, ($C_{1-4}$)alkoxy-($C_{2-4}$)alkylamino-($C_{1-4}$)alkyl, ($C_{1-4}$)alkylthio-($C_{1-4}$)alkyl, hydroxy-($C_{2-4}$)alkylthio-($C_{1-4}$)alkyl, ($C_{1-4}$)alkoxy-($C_{2-4}$)alkylthio-($C_{1-4}$)alkyl, phenoxy-($C_{1-4}$)alkyl, anilino-($C_{1-4}$)alkyl, phenylthio-($C_{1-4}$)alkyl, cyano-($C_{1-4}$)alkyl, halogeno-($C_{2-4}$)alkoxy, hydroxy-($C_{2-4}$)alkoxy, ($C_{2-4}$)alkanoyloxy-($C_{2-4}$)alkoxy, ($C_{1-4}$)alkoxy-($C_{2-4}$)alkoxy, carboxy-($C_{1-4}$)alkoxy, ($C_{1-4}$)alkoxycarbonyl-($C_{1-4}$)alkoxy, carbamoyl-($C_{1-4}$)alkoxy, N—($C_{1-4}$)alkylcarbamoyl-($C_{1-4}$)alkoxy, N, N-di-[($C_{1-4}$)alkyl]carbamoyl-($C_{1-4}$)alkoxy, amino-($C_{2-4}$)alkoxy, ($C_{1-4}$)alkylamino-($C_{2-4}$)alkoxy, di-[($C_{1-4}$)alkyl]amino-($C_{2-4}$)alkoxy, ($C_{2-4}$)alkanoyloxy, hydroxy-($C_{2-4}$)alkanoyloxy, ($C_{1-4}$)alkoxy-($C_{2-4}$)alkanoyloxy, phenyl-($C_{1-4}$)alkoxy, phenoxy-($C_{2-4}$)alkoxy, anilino-($C_{2-4}$)alkoxy, phenylthio-($C_{2-4}$)alkoxy, piperidino-($C_{2-4}$)alkoxy, morpholino-($C_{2-4}$)alkoxy, piperazin-1-yl-($C_{2-4}$)alkoxy, 4-($C_{14}$)alkylpiperazin-1-yl-($C_{2-4}$)alkoxy, halogeno-($C_{2-4}$)alkylamino, hydroxy-($C_{2-4}$)alkylamino, ($C_{2-4}$)alkanoyloxy-($C_{2-4}$)alkylamino, ($C_{1-4}$)alkoxy-($C_{2-4}$)alkylamino, carboxy-($C_{1-4}$)alkylamino, ($C_{1-4}$)alkoxycarbonyl-($C_{1-4}$)alkylamino, carbamoyl-($C_{1-4}$)alkylamino, N—($C_{1-4}$)alkylcarbamoyl-($C_{1-4}$)alkylamino, N, N-di-[($C_{1-4}$)alkyl]carbamoyl-($C_{1-4}$)alkylamino, amino-($C_{2-4}$)alkylamino, ($C_{1-4}$)alkylamino-($C_{2-4}$)alkylamino, di-1($C_{1-4}$)alkyl]amino-($C_{2-4}$)alkylamino, phenyl-($C_{1-4}$)alkylamino, phenoxy-($C_{2-4}$)alkylamino, anilino-($C_{2-4}$)alkylamino, phenylthio-($C_{2-4}$)alkylamino, ($C_{2-4}$)alkanoylamino, ($C_{1-4}$)alkoxycarbonylamino, ($C_{1-4}$)alkylsulphonylamino, benzamido, benzenesulphonamido, 3-phenylureido, 2-oxopyrrolidin-1-yl, 2,5dioxopyrrolidin-1-yl, halogeno-($C_{2-4}$)alkanoylamino, hydroxy-($C_{2-4}$)alkanoylamino, ($C_{1-4}$)alkoxy-($C_{2-4}$)alkanoylamino, carboxy-($C_{2-4}$)alkanoylamino, ($C_{1-4}$)alkoxycarbonyl-($C_{2-4}$)alkanoylamino, carbamoyl-($C_{2-4}$)alkanoylamino, N—($C_{1-4}$)alkylcarbamoyl-($C_{2-4}$)alkanoylamino, N,N-di-[($C_{1-4}$)alkyl]carbamoyl-($C_{2-4}$)alkanoylamino, amino-($C_{2-4}$)alkanoylamino, ($C_{1-4}$)alkylamino-($C_{2-4}$)alkanoylamino or di-[($C_{1-4}$)alkyl]amino-($C_{2-4}$)alkanoylamino moiety.

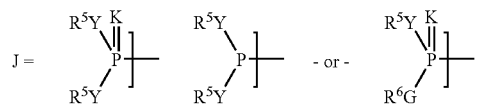

K is O or S;

each occurrence of Y is independently —O—, —S—, —NR—, or a chemical bond;

each occurrence of is independently an aliphatic, heteroaliphatic, aryl or heteroaryl moiety, or (except when attached directly to P) $R^5$ may be H;

each occurrence of $R^6$ is independently $R^5$, -PK($YR^5$)($YR^5$), —$SO_2$($YR^5$) or —C(O)($YR^5$)

wherein two of the $R^5$ and/or $R^6$ moieties may be chemically linked to one another to form a ring;

each occurrence of G is independently —O—, —S—, —NR— or $M_X$;

each occurrence of $M_X$ is independently a 1–6 carbon aliphatic moiety;

each occurrence of R and R', without further alphanumeric designation, is independently hydrogen, or an aliphatic, heteroaliphatic, aryl or heteroaryl moiety; and in each of the foregoing groups each aliphatic or heteroaliphatic moiety contains 1–10 aliphatic carbon atoms and may be branched or unbranched, cyclic or acyclic, substituted or unsubstituted, and may contain one or more electronically unsaturated bonds; and each aryl and heteroaryl moiety may be substituted or unsubstituted.

6. The compound of claim 1 wherein $R^B$ is one of the following structures

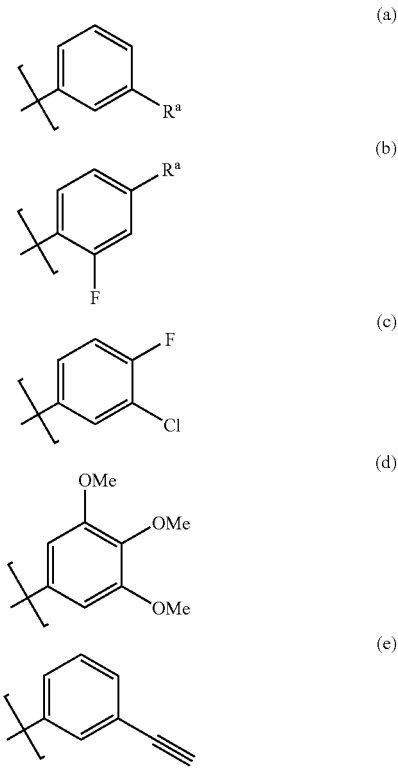

-continued

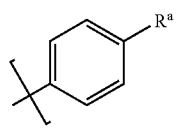 (f)

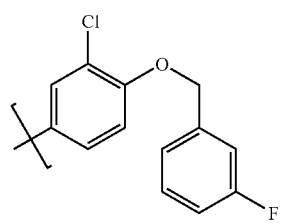 (g)

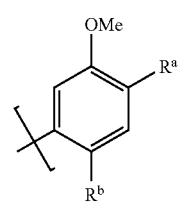 (h)

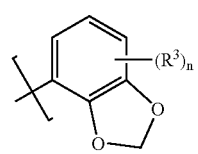 (i)

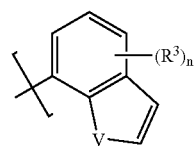 (j)

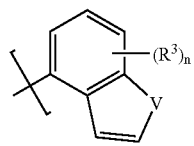 (k)

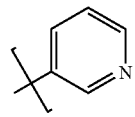 (l)

wherein each $R^a$ and $R^b$ is independently chosen from H, halogen or —$OR^J$; V is O or NH; n is 0, 1, 2 or 3; and each $R^3$ is halogen, trifluoromethyl, cyano, nitro, hydroxy, amino, carboxy, carbamoyl, (1–6C)alkyl, (2–8C)alkenyl, (2–8C)alkynyl, (1–6C)alkoxy, (2–6C)alkenyloxy, (2–6C)alkynyloxy, (1–6C)alkylthio, (1–6C)alkylsulphinyl, (1–6C)alkylsulphonyl, (1–6C)alkylamino, di-[(1–6C)alkyl]amino, (1–6C)alkoxycarbonyl, N-(1–6C)alkylcarbamoyl, N,N-di-[(1–6C)alkyl]carbamoyl, (2–6C)alkanoyl, (2–6C)alkanoyloxy, (2–6C)alkanoylamino, N-(1–6C)alkyl-(2–6C)alkanoylamino, (3–6C)alkenoylamino, N-(1–6C)alkyl(3–6C)alkenoylamino, (3–6C)alkynoylamino, N-(1–6C)alkyl-(3–6C)alkynoylamino, N-(1–6C)alkylsulphamoyl, N,N-di-[(1–6C)alkyl]sulphamoyl, (1–6C)alkanesulphonylamino and N-(1–6C)alkyl-(1–6C)alkanesulphonylamino, or from a group of the formula:

$$—X^6—R^{11}$$

wherein $X^6$ is a direct bond or is O or $N(R^{12})'$ wherein $R^{12}$ is hydrogen or (1–6C)alkyl, and $R^{11}$ is halogeno-(1–6C)alkyl, hydroxy-(1–6C)alkyl, (1–6C)alkoxy-(1–6C)alkyl, cyano-(1–6C)alkyl, amino-(1–6C)alkyl, (1–6C)alkylamino-(1–6C)alkyl or di-[(1–6C)alkyl]amino-(1–6C)alkyl, or from a group of the formula:

$$—X^7\text{-}Q^5$$

wherein $X^7$ is a direct bond or is O, S, SO, $SO_2$, $N(R^{13})$, CO, $CH(OR^{13})$ $CON(R^{13})$, $N(R^{13})CO$, $SO_2N(R^{13})$, $N(R^{13})SO_2$, $C(R^{13})_2O$, $C(R^{13})_2S$ or $N(R^{13})C(R^{13})_2$, wherein $R^{13}$ is hydrogen or (1–6C)alkyl, and $Q^5$ is aryl, aryl-(1–6C)alkyl, heteroaryl, heteroaryl-(1–6C)alkyl, heterocyclyl or heterocyclyl-(1–6C)alkyl which optionally bears 1 or 2 substituents, which may be the same or different, selected from halogeno, (1–6C)alkyl, (2–8C)alkenyl, (2–8C)alkynyl and (1–6C)alkoxy, and any heterocyclyl group within $Q^5$ optionally bears 1 or 2 oxo or thioxo substituents; or a pharmaceutically-acceptable salt thereof.

7. The compound of claim 6 of the formula:

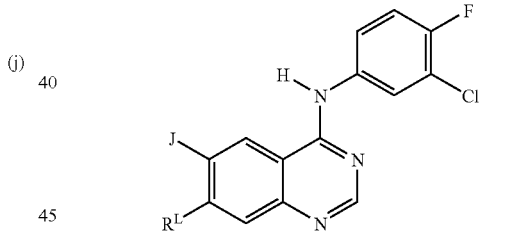

or

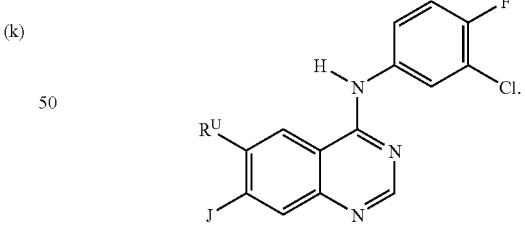

8. The compound of claim 6 of the formula:

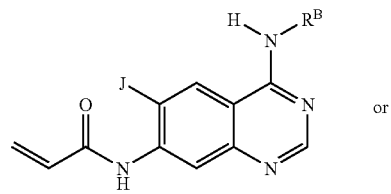

or

-continued
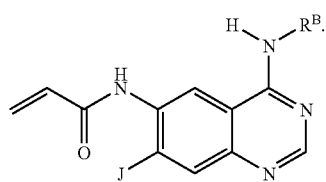
9. The compound of claim 6 of the formula:
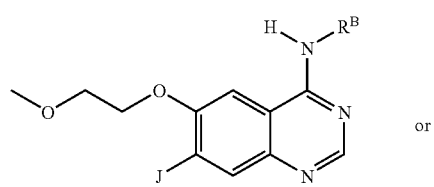
or
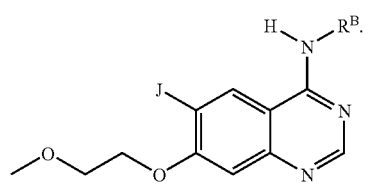
10. The compound of claim 6 of the formula:
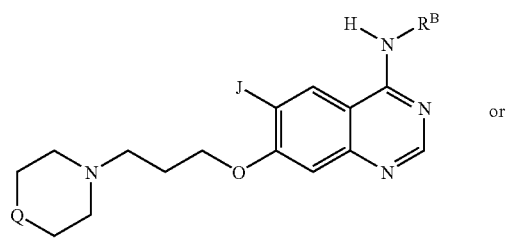
or
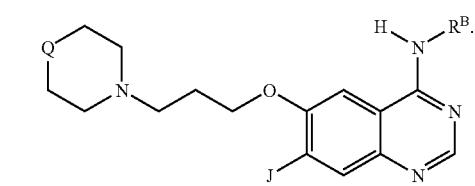
wherein Q is O, NR or CHR.
11. The compound of claim 6 of the formula:
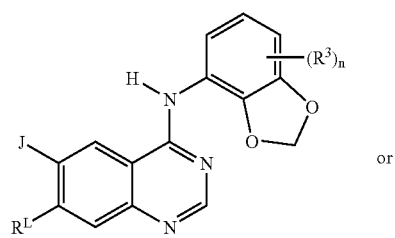
or
-continued
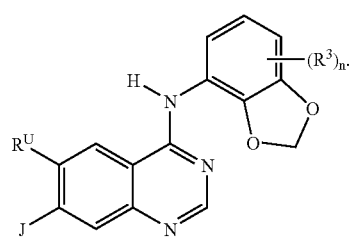
12. The compound of claim 6 of the formula:
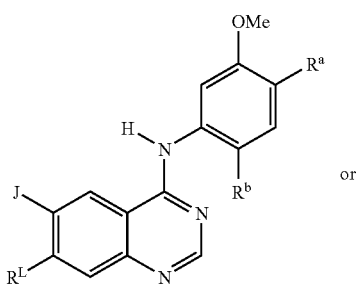
or
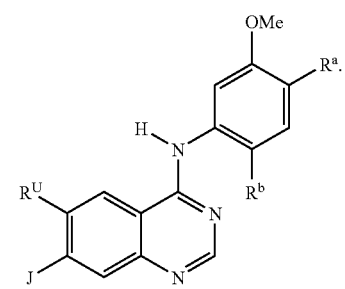
13. The compound of claim 6 of the formula:
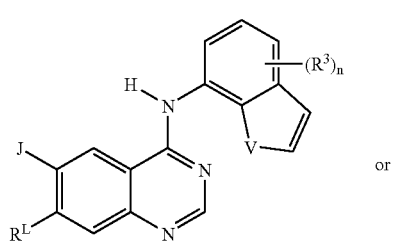
or
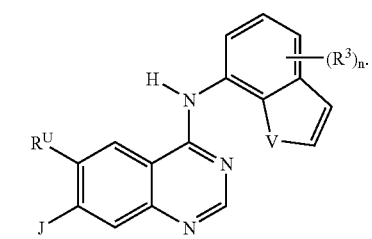

14. The compound of claim 6 of the formula:
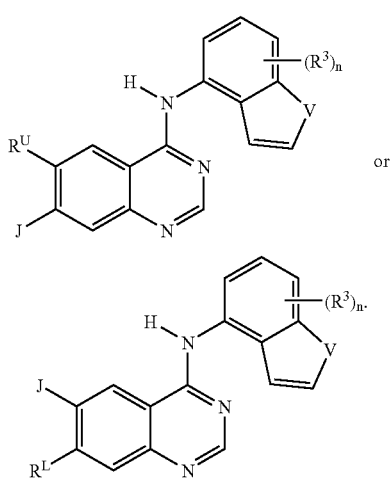
or
15. The compound of any of claims 3–14 in which J is selected from the following:
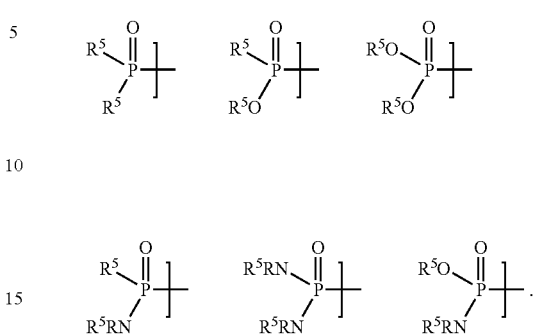
16. A composition comprising a compound of any of claims 1–14 and one or more pharmaceutically acceptable carriers, diluents or other excipients.
* * * * *